(12) United States Patent
Durand et al.

(10) Patent No.: US 8,067,469 B2
(45) Date of Patent: *Nov. 29, 2011

(54) SYSTEM FOR TRAPPING FLYING INSECTS WITH ATTRACTANT LURES

(75) Inventors: Emma A Durand, Jamestown, RI (US); Miao-Yong Cao, Warwick, RI (US); Cuixia Liu, Warwick, RI (US); Richard B. Dunne, Jamestown, RI (US)

(73) Assignee: Woodstream Corporation, Lititz, PA (US)

( * ) Notice: Subject to any disclaimer, the term of this patent is extended or adjusted under 35 U.S.C. 154(b) by 1321 days.

This patent is subject to a terminal disclaimer.

(21) Appl. No.: 10/864,284

(22) Filed: Jun. 8, 2004

(65) Prior Publication Data

US 2005/0019361 A1 Jan. 27, 2005

Related U.S. Application Data

(63) Continuation-in-part of application No. 10/431,586, filed on May 8, 2003, now Pat. No. 7,074,830.

(60) Provisional application No. 60/378,369, filed on May 8, 2002.

(51) Int. Cl.
*A01N 37/36* (2006.01)
*A01N 25/04* (2006.01)

(52) U.S. Cl. .......... 514/557; 514/772; 514/944; 424/84; 424/405; 424/484

(58) Field of Classification Search .................. 514/557, 514/772, 944; 424/84, 405, 484
See application file for complete search history.

(56) References Cited

U.S. PATENT DOCUMENTS

| | | | |
|---|---|---|---|
| 1,693,368 A | 11/1928 | Cherry | |
| 2,893,161 A | 7/1959 | Reid | |
| 4,249,673 A | 2/1981 | Katoh et al. | |
| 4,506,473 A | 3/1985 | Waters, Jr. | |
| 4,519,776 A | 5/1985 | Deyoreo et al. | |
| 4,608,774 A | 9/1986 | Sherman | |
| 4,785,573 A | 11/1988 | Millard | |
| 4,802,303 A | 2/1989 | Floyd, III | |
| 5,157,865 A | 10/1992 | Chang | |
| 5,167,090 A | 12/1992 | Code | |
| 5,189,830 A | 3/1993 | Montemurro | |
| 5,205,064 A | 4/1993 | Nolen | |
| 5,205,065 A * | 4/1993 | Wilson et al. | 43/113 |
| 5,238,681 A | 8/1993 | Chang et al. | |
| 5,255,468 A | 10/1993 | Cheshire, Jr. | |
| 5,311,697 A | 5/1994 | Cavanaugh et al. | |
| 5,329,725 A | 7/1994 | Bible | |
| 5,382,422 A | 1/1995 | Dieguez et al. | |
| 5,417,009 A | 5/1995 | Butler et al. | |
| 5,490,349 A | 2/1996 | Muramatsu | |
| 5,501,033 A | 3/1996 | Wefler | |
| 5,595,018 A | 1/1997 | Wilbanks | |
| 5,647,164 A | 7/1997 | Yates | |
| 5,651,211 A | 7/1997 | Regan et al. | |
| 5,657,576 A | 8/1997 | Nicosia | |
| 5,669,176 A | 9/1997 | Miller | |
| 5,716,634 A | 2/1998 | Tseng et al. | |
| 5,916,918 A | 6/1999 | Konishi et al. | |
| 6,050,025 A | 4/2000 | Wilbanks | |
| 6,055,766 A | 5/2000 | Nolen et al. | |
| 6,083,498 A * | 7/2000 | Landolt | 424/84 |
| 6,132,203 A | 10/2000 | Masin | |
| 6,145,243 A * | 11/2000 | Wigton et al. | 43/139 |
| 6,201,012 B1 * | 3/2001 | Lowndes et al. | 514/460 |
| 6,242,509 B1 | 6/2001 | Berger et al. | |
| RE37,263 E | 7/2001 | Kross et al. | |
| 6,272,790 B1 * | 8/2001 | Paganessi et al. | 43/107 |
| 6,286,249 B1 | 9/2001 | Miller et al. | |
| 6,532,695 B1 | 3/2003 | Alvarado | |
| 6,594,947 B2 | 7/2003 | Lingren et al. | |
| 6,655,080 B2 | 12/2003 | Spiro et al. | |
| 6,662,489 B2 | 12/2003 | Spiro et al. | |
| 6,718,685 B2 | 4/2004 | Bossler | |
| 2003/0084604 A1 | 5/2003 | Durand et al. | |
| 2003/0154643 A1 | 8/2003 | Spiro et al. | |
| 2003/0154645 A1 | 8/2003 | Spiro et al. | |
| 2003/0208951 A1 | 11/2003 | Bossier | |
| 2004/0001870 A1 | 1/2004 | Durand et al. | |
| 2004/0068932 A1 | 4/2004 | Stewart | |
| 2004/0139648 A1 | 7/2004 | Durand et al. | |
| 2005/0019361 A1 | 1/2005 | Durand et al. | |

FOREIGN PATENT DOCUMENTS

| | | | |
|---|---|---|---|
| GB | 2356141 A * | 5/2001 | |
| JP | 1-4128 | 4/1989 | |
| JP | 2-63679 | 5/1990 | |
| JP | 5-39335 | 2/1993 | |
| WO | 03/028448 | 4/2003 | |
| WO | WO 2004/028247 | 4/2004 | |

OTHER PUBLICATIONS

Geier et al., Chemical Senses 24: 647-653, 1999.*
Megalomania, The Preparation of Ammonia [online],2002 [retrieved on Sep. 30, 2008]. Retrieved from the Internet: <URL: http://web.archive.org/web/20021021064749/http://www.totse.com/en/technology/science_technology/166763.html>.*
Takeyama et al., UV-Curable Gel Bases and Their Compositions for Retaining Volatile, Chemical Abstracts 119: 118743 (1993).

(Continued)

Primary Examiner — Fereydoun G Sajjadi
Assistant Examiner — Courtney Brown
(74) Attorney, Agent, or Firm — Jacobson Holman PLLC

(57) ABSTRACT

The present application discloses a system for trapping flying insects, a first chemical lure such as lactic acid, a salt of lactic acid, or combinations thereof, and a second chemical lure comprising a source of ammonia. The lures may be employed in particular geometric shapes contained in specifically designed housing to ensure an effective release rate over extended periods of time.

81 Claims, 8 Drawing Sheets

OTHER PUBLICATIONS

Acree et al., 1-Lactic Acid: a Mosquito Attractant Isolated from Humans, Chemical Abstracts 69: 94388 (1968).
Geier, A New Y-Tube Alfactometer for Mosquitoes to Measure the Attractiveness of Host Odours, CROPU Abstract 1999-87418 (1999).
Bosch et al., "Contribution of Fatty Acids to Olfactory Host Finding of Female *Aedes Aegypti*," *Chem. Senses*, vol. 25, pp. 323-330, 2000.
Braks et al., "Incubated Human Sweat But Not Fresh Sweat Attracts the Malaria Mosquito *Anopheles gambiae* Sensu Stricto," *Journal of Chemical Ecology*, vol. 25, No. 3, pp. 663-672, 1999.
Braverman et al., "Attractiveness of Vertebrate Hosts to Culex pipiens (Diptera: Culicidae) and Other Mosquitoes in Israel," *Journal of Medical Entomology*, vol. 28, No. 1, pp. 133-138, Jan. 1991.
Dekker et al., "L-Lactic Acid: A Human-Signifying Host Cue for the Anthropophilic Mosquito Anopheles Gambiae," *Medical and Veterinary Entomology*, vol. 16, pp. 91-98, 2002.
Geier et al., "Ammonia as an Attractive Component of Host Odour for the Yellow Fever Mosquito, *Aedes aegypti*," *Chem. Senses*, vol. 24, pp. 647-653, 1999.
Jacobson et al., "Chemical Insect Attractants," *Science*, vol. 140, No. 3574, pp. 1367-1374, Jun. 28, 1963.
Wieting et al., "The Olfactory Responses of Flies in a New Type of Insect Olfactometer," *Journal of Economic Entomology*, vol. 32, No. 1, pp. 24-29, Feb. 1939.
Owners Manual Bug Vac Model 1101, Mar. 17, 2003.
Mosquito Ecology Field Sampling, 2nd ed., p. 500, 502, 517, 524, 546-547 (1993).
Carestia et al., "Effectiveness of Carbon Dioxide as a Mosquito Attractant in the CDC Miniature Light Trap," *Mosquito News*, 27(1):90-92 (1967).
Dipteran Collection equipment folder, American Biophysics Corp., Jul. 1994.
Burkett et al., "Light, Carbon Dioxide, and Octenol-Baited Mosquito Trap and Host-Seeking Activity Evaluations for Mosquitoes in a Malarious Area of the Republic of Korea," *J. Am. Mosquito Control Assn.*, 17(3):196-205 (2001).
Floore et al., "Mosquito Trapping Studies to Determine Efficacy of Two Models of the Flowtron® Mosquito Luring Device," *J. Florida Anti-Mosquito Assn.*, 56(1):13-17 (1985).
Grant et al., "Electrophysiological responses of receptor neurons in mosquito maxillary palp sensilla to carbon dioxide," *J. Comp. Physiol. A.* 177:389-396 (1995).
Kline, "Comparison of Two American Biophysics Mosquito Traps: The Professional and a New Counterflow Geometry Trap," *J. American Mosquito Control Assn.*, 15 (3):276-282 (1999).
Kubis, Database CAPLUS on STN, Am. Chemical Society, Columbus OH, Accession No. 2001:256247, PL177390, abstract, 1995.
Mboera et al., "Comparison of carbon dioxide-biated trapping systems for sampling outdoor mosquito populations in Tanzania," *Medical and Veterinary Entomology*, 14:257-263 (2000).
Peterson et al., "Studies of the Responses of the Female *Aedes* Mosquito," Dept. of Zoology, University of Western Ontario, London, Canada, pp. 535-541 (1951).
Service, "Sampling Adults by Animal Bait Catches and by Animal-Baited Traps," Mosquito Ecology Field Sampling Methods, Ch. 5, $2^{nd}$ ed. p. 349-498 (1995).
Service, "Sampling Adults with Carbon Dioxide Traps, Light-Traps, Visual Attraction Traps and Sound Traps," Mosquito Ecology Field Sampling Methods, Ch. 6, $2^{nd}$ ed., p. 499-610 (1995).
Sudia et al., "Battery-Operated Light Trap, An Improved Model," *J. Am. Mosquito Control Assn.*, 4(4):536-538 (1988).
Lentek MKO1 "Original" Mosquito Trap, www.uniquedistributors.com/mosquitotrap.html.
Flying Insects, www.doktordoom.com/flying.html (Mar. 29, 2004).
Ammonia—Wikipedia, http://en.wikipedia.org/wiki/Ammonia (Mar. 29, 2004).
The Preparation of Ammonia by Megalomania, www.totse.com/en/technology/science_technology/166763.html (Mar. 29, 2004).

* cited by examiner

SYSTEM FOR TRAPPING FLYING INSECTS WITH ATTRACTANT LURES

CROSS REFERENCE TO RELATED APPLICATIONS

This application is a continuation-in-part of application Ser. No. 10/431,586, filed May 8, 2003, now U.S. Pat. No. 7,074,830 which in turn claims priority of U.S. Provisional Application Ser. No. 60/378,369, filed May 8, 2002, the contents of each of which are incorporated herein by reference in their entirety.

SUMMARY OF THE INVENTION

The present invention relates to attractant lures for trapping flying insects, such as mosquitoes, no-see-ums, and other insects that are attracted to components of sweat and breath emanating from mammals, and systems related thereto.

According to one embodiment of the invention a lure for attracting flying insects includes a source of ammonia gas and a source of lactic acid, wherein the sources of ammonia gas and lactic acid are housed in physical separation from each other prior to use.

Another embodiment of the invention is a lure for attracting flying insects comprising a first chemical attractant and a second chemical attractant where the first chemical attractant comprises a solution of lactic acid in a carrier wherein the carrier is a polymeric gel, plastic, polymer, or a porous material such as a porous ceramic rod or frit and the second chemical attractant comprises a source of ammonia; wherein the first and second attractants are physically isolated from each other prior to use of the lure.

Another embodiment of the invention is a lure for attracting flying insects comprising a first chemical attractant and a second chemical attractant where the first chemical attractant comprises a solution of lactic acid and the second chemical attractant comprises a source of ammonia; wherein the first and second attractants are physically isolated from each other prior to use of the lure and further wherein the lure is capable of providing an effective amount of the first and second chemical attractants continuously or intermittently for at least an extended period of time of use wherein the extended period of time is at least one week, two weeks, three weeks, four weeks, six weeks, eight weeks, ten weeks, or twelve weeks.

Another embodiment of the invention is a lure for attracting flying insects comprising a first chemical attractant and a second chemical attractant where the first chemical attractant comprises a solution of lactic acid and the second chemical attractant comprises a source of ammonia; wherein the first and second attractants are physically isolated from each other prior to use of the lure and wherein the lure is at least 50% more effective in attracting insects than a comparable lure where the comparable lure may comprise one but not both of the first and second chemical attractants, octenol, carbon dioxide or other attractant.

Another embodiment of the invention is a system for separately generating ammonia, lactic acid and $CO_2$ in situ and supplying them in configurations attractive to flying insects.

Another embodiment of the invention is the use of a first lure comprising lactic acid, a second lure comprising ammonium bicarbonate, each of the first and second lures being provided in liquid, semi-solid or solid form, for the attraction of flying insects, wherein the first and second lures are maintained in physical isolation from each other until just prior to use and wherein during use contact of the first and second lures with an ambient temperature or warm gas flow will cause ammonia gas to be generated and diffuse from the ammonium bicarbonate of the second lure and will cause lactic acid to be generated and diffused from the first lure, thereby forming an attractant mixture for luring flying insects.

According to another embodiment of the invention a device for attracting flying insects comprises a device for producing gaseous $CO_2$, in situ, an exhaust port for releasing the gaseous $CO_2$, an inlet port for introducing flying insects, a chamber communicating with and accessible from the inlet port for trapping insects, and at least two chemical lures, wherein a first lure comprises a solution of lactic acid and a UV-reactive compound and a second lure comprises a source of ammonia gas, wherein the first and second lures are stored to prevent contact there between until just prior to use.

Other embodiments, features and advantages of this invention will become apparent from the following detailed description when taken in conjunction with the accompanying drawings, which are a part of this disclosure and which illustrate, by way of example, principles of this invention.

DETAILED DESCRIPTION OF EMBODIMENTS OF THE INVENTION

Figure 1:
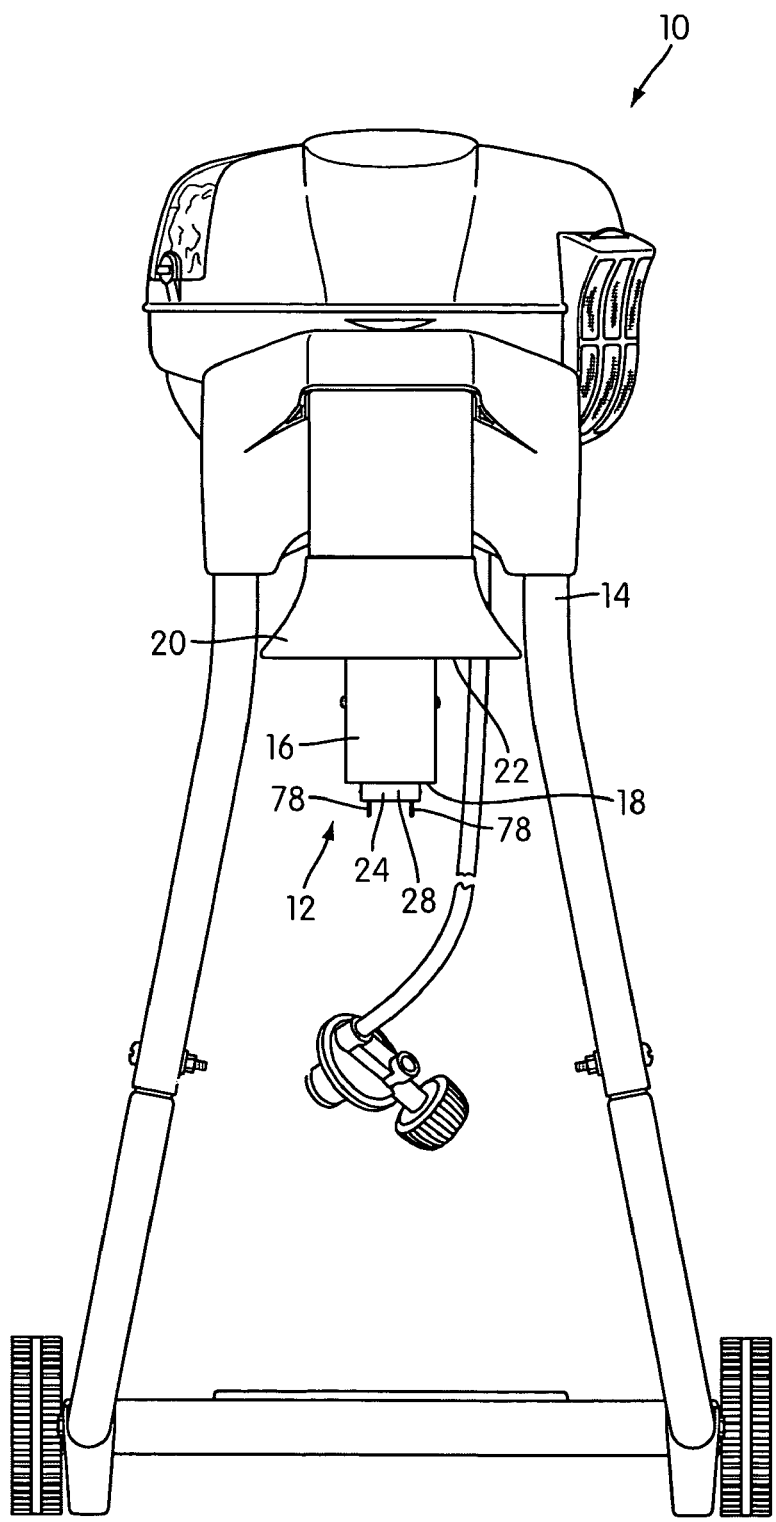
FIG. 1 is a front elevational view of an exemplary insect trapping apparatus with an attractant system constructed in accordance with one embodiment of the invention mounted thereto.
Figure 2:
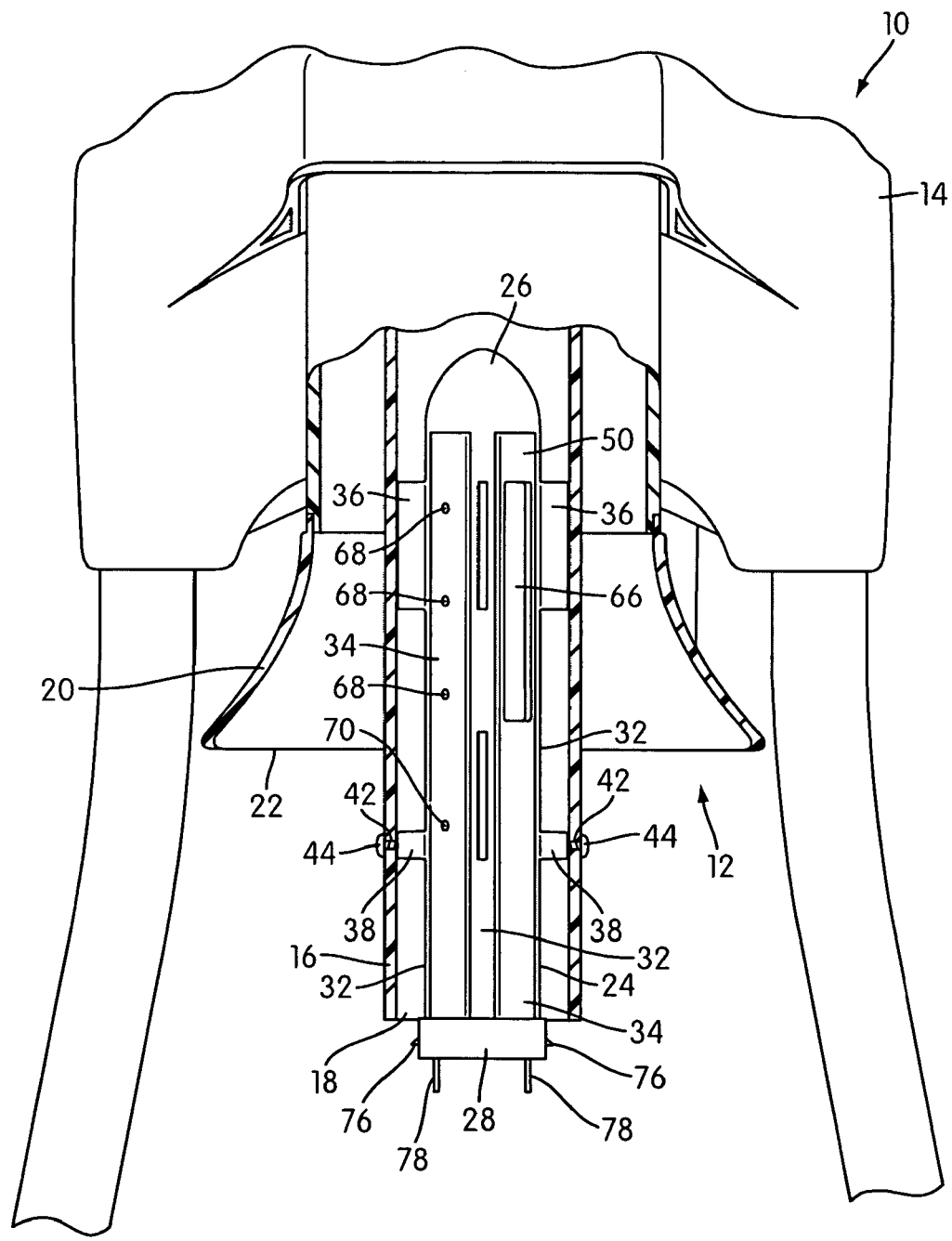
FIG. 2 is a partial cross-section of the inlet and outlet tubes of the apparatus in FIG. 1, the cross-section showing the receptacle and attractant system.
Figure 3:
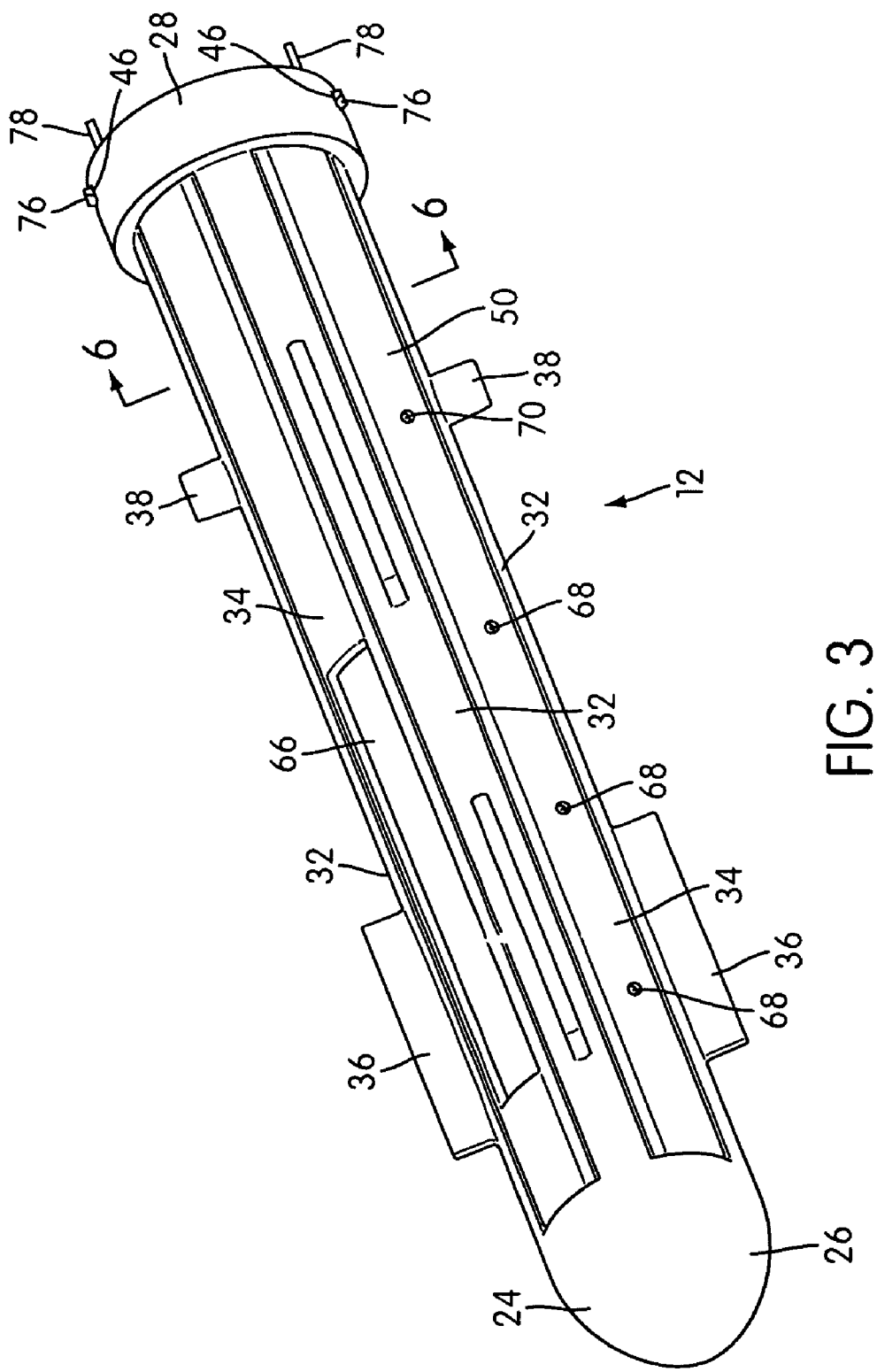
FIG. 3 is a perspective view of the receptacle and the attractant system with the attractant system inserted longitudinally into the receptacle.
Figure 4:
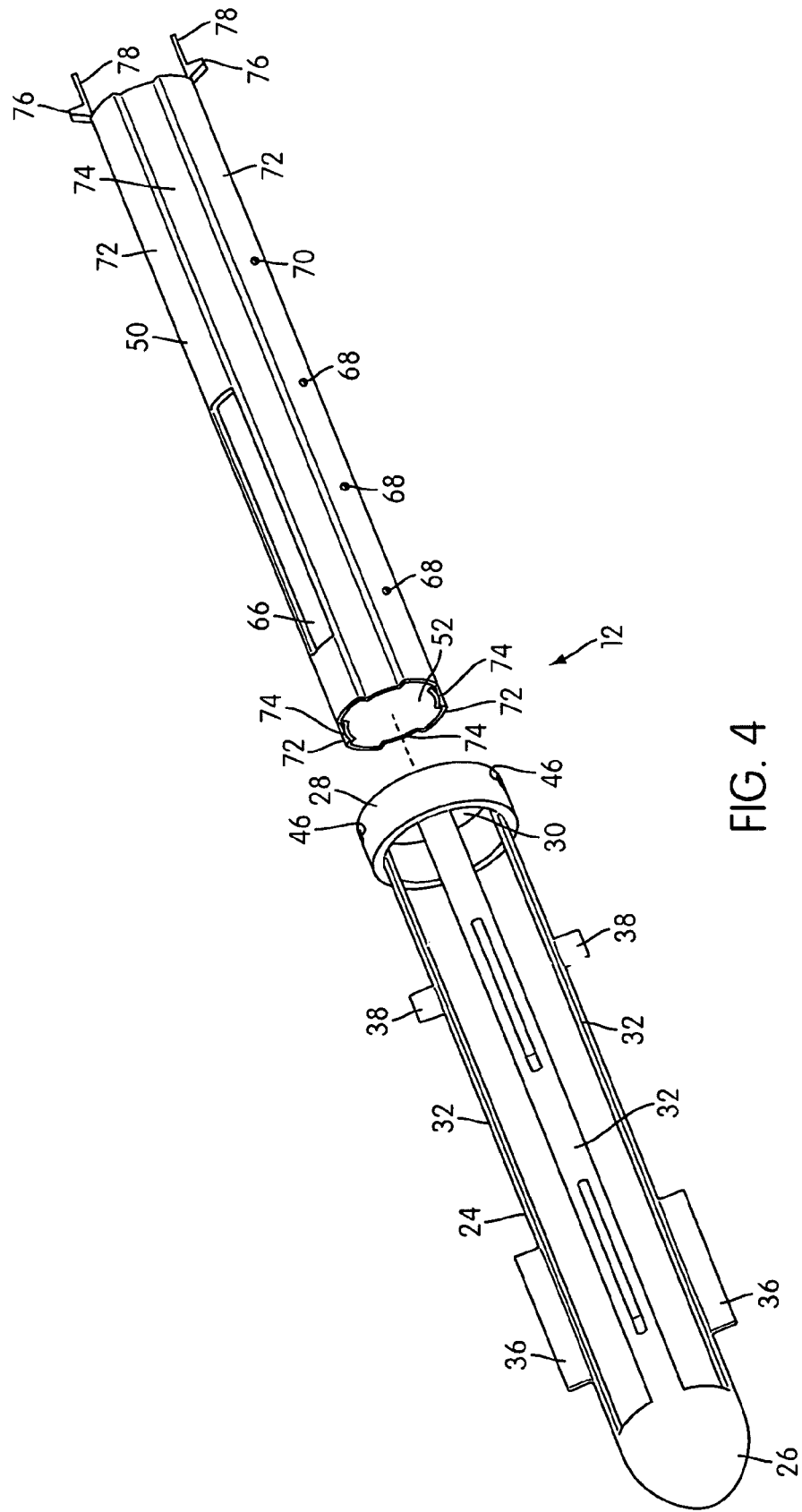
FIG. 4 is a perspective view of the receptacle and the attractant system with the attractant system withdrawn from the receptacle.
Figure 5:
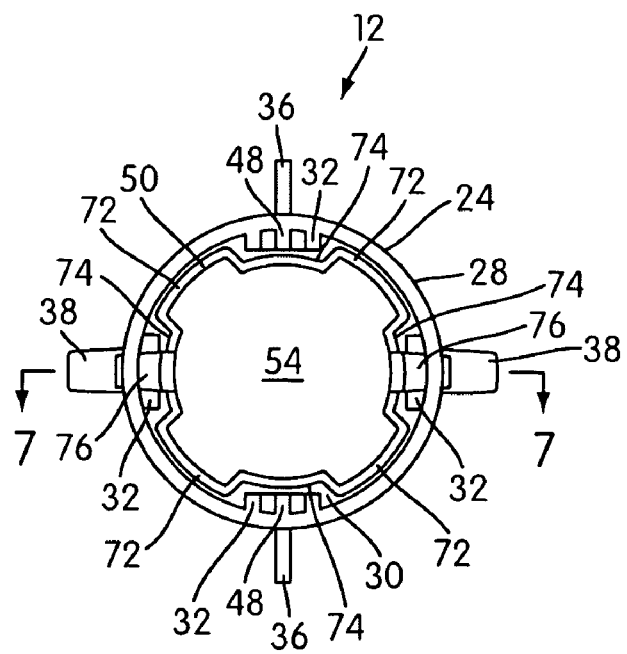
FIG. 5 is a bottom end view of the attractant system inserted longitudinally into the receptacle.
Figure 6:
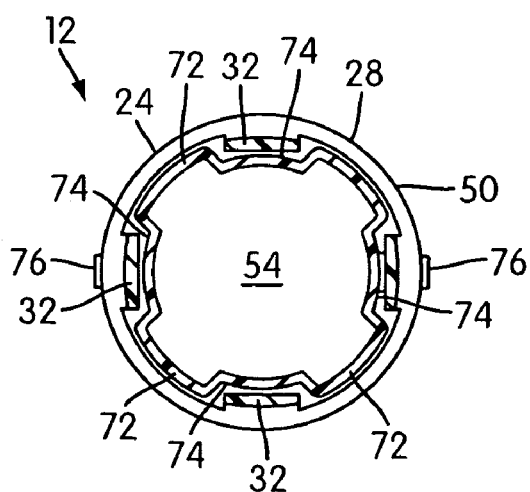
FIG. 6 is a cross-section taken along line 6-6 in FIG. 3.
Figure 7:
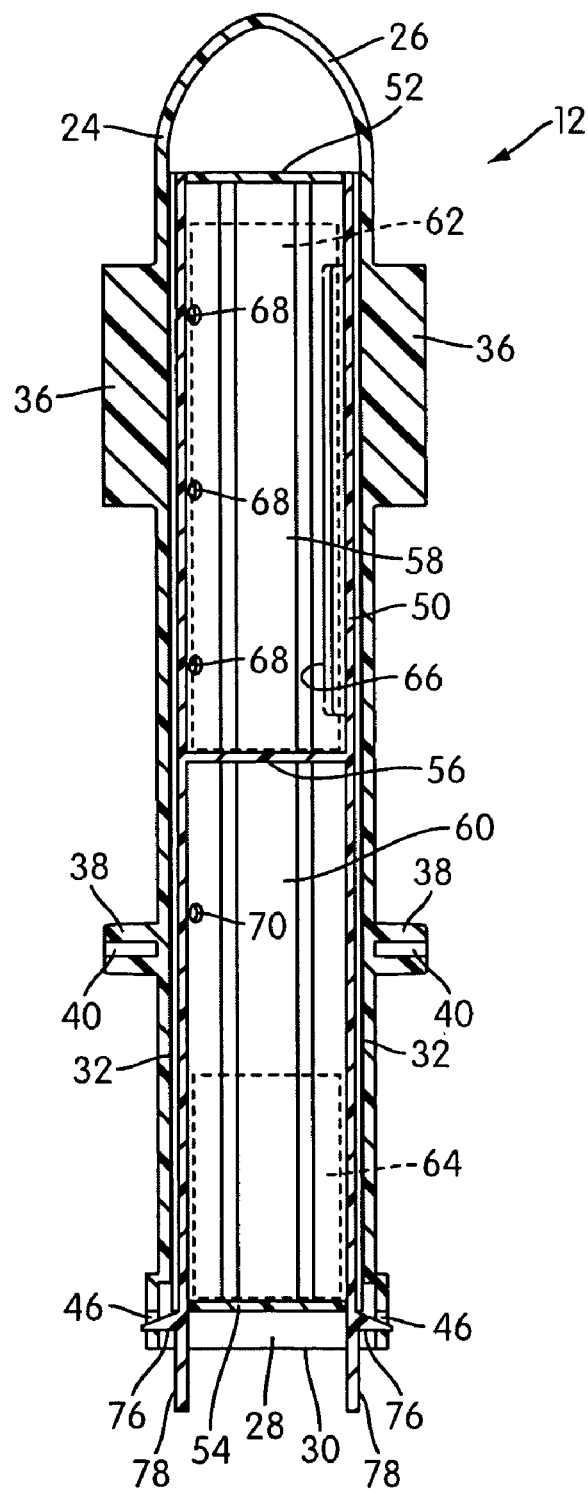
FIG. 7 is a cross-section taken along line 7-7 in FIG. 5.
Figure 8:
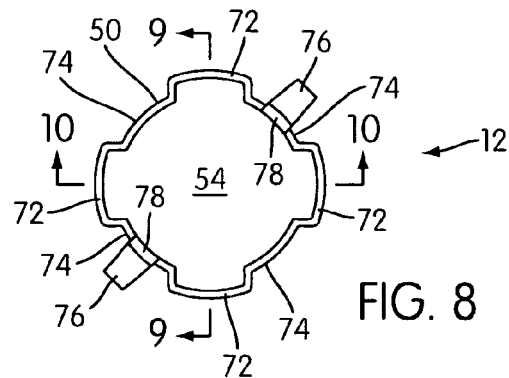
FIG. 8 is a bottom end view of the attractant system.
Figure 9:
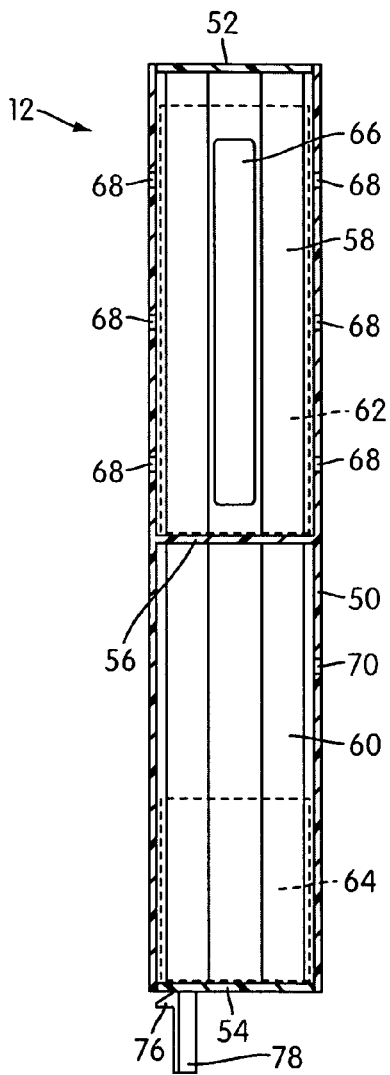
FIG. 9 is a cross-section taken along line 9-9 of FIG. 8.
Figure 10:
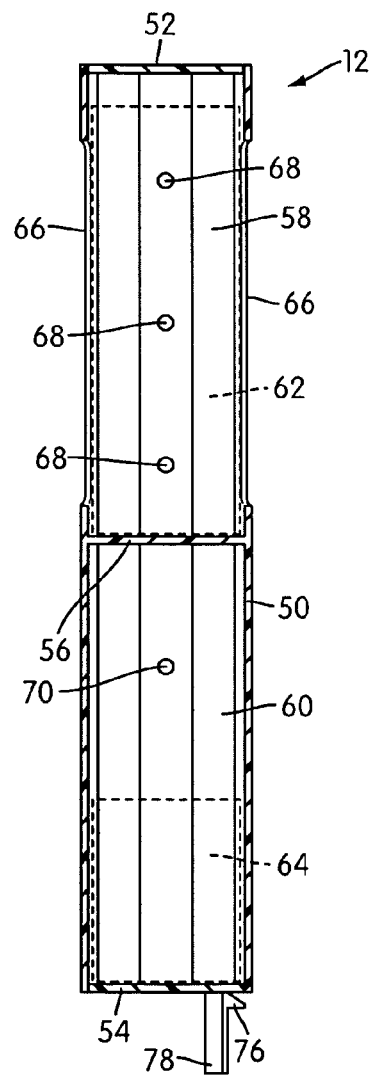
FIG. 10 is a cross-section taken along line 10-10 of FIG. 9.

As used herein, the term "chemical lure" is intended to mean a liquid, semi-liquid (e.g., gel, polymeric gel, hydrogel or other colloid), or solid chemical formulation from which an attractant compound that mimics the attractive character of at least one exudate of a human or other mammal, such as sweat or wound fluid, may be emitted in a manner effective to attract the desired insect, such as a flying insect, for example, mosquitoes. Such chemical lures may be isolated natural compounds, such as isoforms of lactic acid, or may be a synthetic compound engineered to exhibit the attractive characteristics of the components of human exudates. Other attractants include, for example, proteinaceous compounds and organic acids. In an exemplary embodiment of the invention each of $CO_2$, lactic acid and ammonia are used in admixture as the chemical lure for attracting a wide range of flying insects.

In an exemplary embodiment of the invention, a chemical lure comprising each of $CO_2$, lactic acid and ammonia, wherein the $CO_2$ gas is generated in situ in the form of a flowing gas plume into which the lactic acid and ammonia are diffused from respective sources thereof, is used in a system designed to attract mosquitoes and other flying insects, including, but not limited to, *Aedes aegypti, Aedes albopictus, Aedes vexans, Anopheles atropos, Anopheles crucians, Anopheles punctipennis, Anopheles walkeri, Culex erraticus, Culex nigripalpus, Culex pipiens, Culex quinquefasciatus, Culex salinarius, Culiseta melanura, Ochlerotatus canadensis, Ochlerotatus fulvus-pallens, Ochlerotatus infirmatus, Ochlerotatus intrudens, Ochlerotatus triseriatus,* and *Psorophora ferox*.

In another exemplary embodiment of the invention a lure comprising a source of lactic acid and a source of ammonia is provided such that an insect attracting amount of lactic acid and ammonia may be supplied by the lure to a gas carrier. The lure may be designed to provide release rates of lactic acid and ammonia suitable for indoor uses or outdoor uses.

Lures of the invention may be housed such that the lactic acid source and the ammonia source are physically separated from each other prior to use to reduce degradation of the attractants during storage. Preferably, a removable seal is provided with the lure such that removal of the seal permits release of the lactic acid and ammonia into a gas carrier.

The gas carrier to which lactic acid and ammonia may be supplied by the lures of the invention may be ambient air, warm and/or moist air, a gas stream containing an elevated level of carbon dioxide, an exhaust plume from combustion of a fuel such as a hydrocarbon-based fuel, or other gas. The carrier gas in different embodiments may be flowing or may move passively by means such as diffusion or convection. Flowing gas streams may optionally be provided by combustion sources, fans, or other methods for creating pressure differentials. Separate gas carriers may be used to receive the lactic acid and ammonia or the same gas carrier may be used to receive both chemical attractants. In certain embodiments of the invention the lure may be configured to supply lactic acid and ammonia to a gas carrier containing elevated levels of carbon-dioxide gas, whereas in other embodiments the lure may be combined with a source of carbon-dioxide gas but release the carbon dioxide gas separately from the lactic acid and/or ammonia.

Lures of the invention are effective for attracting flying insects. In some embodiments of the invention, effectiveness may be demonstrated by use of a lure of the invention to attract one or more species of flying insects. In certain embodiments of the invention, the lure of the invention demonstrates superior effectiveness in attracting flying insects or specific species of flying insects in comparison with other lures omitting one of the chemical attractants of the lure of the invention or in comparison with known attractants such as octenol or carbon dioxide. Certain embodiments of the invention show improved effectiveness in comparison with such other attractants such that the lures of the invention in comparison testing may attract 50% more, 100% more, 200% more, 300% more, 400% more, or 500% more flying insects or flying insects of certain selected species of flying insect. Testing of improved effectiveness may be accomplished through cage testing or preferably in application outdoors where the positions of the attractants being compared are rotated to reduce the effect of environmental effects upon the comparison. For example a Latin square type sampling protocol may be employed or other suitable sampling technique may be used. Preferably, such outdoor tests are conducted for an extended period of time for one, two, or several days and total catches of insects over the testing period are compared. In certain preferable embodiments of the invention, the lures of the invention demonstrate effectiveness for extended periods of time of one week, two weeks, three weeks, four weeks, six weeks, eight weeks, ten weeks, twelve weeks or similar time periods. When comparing the effectiveness of lures and devices of the invention for extended periods of time, the lures of the invention and the comparison lures may be tested for the entire extended period or by sampling one or more times for shorter periods such as one, two or three days over the course of the extended period.

Some embodiments of the invention are effective in attracting flying insects of the species *Aedes aegypti, Aedes albopictus, Aedes vexans, Anopheles atropos, Anopheles crucians, Anopheles punctipennis, Anopheles walkeri, Culex erraticus, Culex nigripalpus, Culex pipiens, Culex quinquefasciatus, Culex salinarius, Culiseta melanura, Ochlerotatus canadensis, Ochlerotatus fulvus-pallens, Ochlerotatus infirmatus, Ochlerotatus intrudens, Ochlerotatus triseriatus,* and *Psorophora ferox* Certain embodiments are preferably more effective in attracting one or more of these species of flying insect than a comparison lure of lactic acid alone, ammonia alone, carbon dioxide alone, lactic acid plus carbon dioxide, ammonia plus carbon dioxide, octenol, or octenol plus carbon dioxide. Preferably such embodiments are measurably 50% more effective than such comparison lures. More preferably they are 100%, 200%, 300%, 400%, 500%, or more effective than such comparison lures.

As used herein, the term "visual lure" is intended to mean a device arranged and configured to visually entice flying insects, attracted to the vicinity of a flying insect trapping device-via a $CO_2$ plume, to fly near an insect inlet port. Visual lures may combine both color and geometric features designed to mimic the visual cues flying insects utilize in targeting a host mammal.

Chemical lures may be engineered and configured to control the amount of compound released over time, thereby ensuring a level of dispersed attractant for effective insect trapping. Lures are generally fashioned to provide highly effective chemical attractants having controlled release into the atmosphere wherein the rate of release may be influenced by the relationship between environmental temperature, humidity, prevailing air currents, other local micro-climate parameters, exhaust/$CO_2$ velocity, and the volatility of the attractant compound. Additionally, where used indoors, the volume of the interior space and the rate of air exchange with outdoor air also influences the desired rate of release of chemical lures.

In an embodiment of the present invention, the release rates of each component of a mixture of chemical lures, e.g., lactic acid, and ammonia ($NH_3$), in a flowing warm stream of air or $CO_2$ gas, are controlled, at least in part, by selection and/or control of the exposed surface of a source of lactic acid and a source of ammonia, with which the flowing stream comes into contact during use, such that the mixture of each of the chemical attractants remains effective to attract flying insects over an extended period of use, such as at least about 2 or 3 weeks or more.

In an embodiment of the present invention, the chemical lure comprises at least one attractant compound that is relatively non-toxic, or displays reduced toxicity compared with traditional insecticides, and is formulated to mimic the natural insect attractants released by mammalian systems. Organic acids and their derivatives are suitable mimics in this regard. Blends of attractants may also be used. These kairomones may be natural compounds found in nature or may be synthetically engineered.

One example of a suitable organic acid and its derivative is lactic acid in free acid form, salts of lactic acid, and combinations thereof. Ammonium lactate is an exemplary lactic acid salt suitable for use as an attractant according to the invention. Ammonia, acetone, uric acid, butyric acid, dimethyldisulfide, 2-phenylethanol and derivatives thereof are also acceptable attractants for many flying insects. Various compounds known to be kairomones are disclosed in Park et al., *J. Insect Physiol.* 45, 85-91, 1999, the contents of which are incorporated in their entirety herein by reference. Lures may be formulated to specifically attract certain species of flying insects known to infest a given region.

In one embodiment of the present invention, the attractant is a food grade form of lactic acid or lactic acid having at least 99% purity in order to reduce the effect of impurities on air quality in the vicinity of the lure when in use. L(+)-lactic acid may be employed either alone or in combination with an additional attractant lure. In another embodiment, the L(+)-lactic acid may be used concurrently as a mixture with calcium lactate. In another embodiment, L(+)-lactic acid alone or in combination with calcium lactate, is used in conjunction with ammonia, such as an aqueous solution of ammonium hydroxide, powdery ammonium bicarbonate or other ammonium compound capable of generating ammonia, such as may occur at ambient temperature, moderately elevated temperature, e.g., above ambient temperature, such as, for example, at least about 85° F. However, it should be understood that chemical lures of the invention may be designed to release ammonia at any desired range of temperatures. One or more chemical lures may be employed, either housed in a single housing, or from multiple separate sources, within or otherwise associated with an insect trap.

Chemical lures may be formulated as liquids, semi-solids, such as gels, or solids, for use with an insect trapping device, such as the devices described herein. Insect trapping devices are well known in the art. For example, American Biophysics Corporation sells insect trapping apparatuses under the trademark MOSQUITO MAGNET that use combustion to generate a $CO_2$ laden outflow for attracting insects. Reference may be made to U.S. Pat. No. 6,145,243 and U.S. Patent Application No. 2003/0084604 A1 for details of the operation of such traps, the entirety of each of which is hereby incorporated into the present application by reference.

In one embodiment of the invention, solid lures are in powder form. The powder may be used as such, for example, stored in a porous bag or envelope, which allows inflow and outflow of a gas stream, or the powder may be compressed or molded into various shapes, such as bricks, plugs or pellets. Solid insect lures may have controlled release rates. In one embodiment, powdered L(+)-lactic acid is compressed into a bullet or cylindrical shape. Whatever the shape or physical form, attractant is released from the liquid, semi-solid or solid lure upon exposure to an air or gas stream at a slightly elevated temperature. In one embodiment a warm, moist $CO_2$-containing exhaust stream, such as from an insect trapping device, is caused to contact at least a portion of the surface of the chemical attractant or attractants, thereby causing diffusion of the chemical attractants, such as lactic acid and ammonia, into the exhaust stream.

According to an embodiment of the invention liquid lures may be used as the chemical attractant. Liquid lures may be used as such in a suitable container or vessel which has one or more openings or passages to allow inflow and outflow of a gas stream but which does not allow inflow or outflow of the liquid. In an alternative embodiment the liquid lure is impregnated onto carriers, such as porous rods or frits, which then release the attractant compound upon exposure to air or other suitable gas, such as the above-mentioned carbon dioxide containing exhaust stream. Any suitable carrier capable of releasably holding a liquid chemical attractant may be employed. In some embodiments of the invention, liquid lactic acid at a concentration of about 1.5 g to about 4.5 g per gram of carrier frit (preferably about 3.5 g to about 4.5 g per gram of carrier frit or alternatively about 1.9 g to about 2.5 g per gram of carrier frit) is used as chemical attractant alone or in combination with one or more additional attractants. When subjected to a $CO_2$ exhaust stream at a temperature of ambient up to about 15° F. above ambient air temperature, such as about 3° F., about 5° F., about 8° F., about 110° F., about 12° F. or about 15F, above ambient air temperature, the lactic acid will be diffused from the attractant. Of course, higher temperatures of the exhaust stream may also be used. On the other hand, it is also within the scope of the invention, such as, when designed for use in particularly warm climates, to use an exhaust gas stream which is at the ambient temperature or only slightly above ambient temperature, depending on the nature of the lure and the desired diffusion rate. Suitable temperatures for any particular environment may be readily determined by routine procedures within the skill of the artisan. Furthermore, these concentrations may be optimized for a given environment.

Diffusion of ammonia from a loose or compressed powdery or granular ammonium bicarbonate may conveniently be achieved by contacting at least a part of the surface of the lure with gas, e.g., air or $CO_2$ gas (or $CO_2$ containing exhaust), at a temperature of from about ambient temperature (or preferably from about 85° F.) to about 140° F. (or preferably about 115° F.), or another temperature range which is also effective for the diffusion of lactic acid from the lactic acid lure, such as a solution of lactic acid in a polymer gel. An outflow gas temperature in the range of from about 85° F. to about 140° F. is generally effective for generating lactic acid and ammonia from most sources of these attractants, including, for example, a lactic acid/gel as described for various embodiments of the invention, and ammonium bicarbonate.

Chemical attractants may be loaded into cartridges to better control release rate of the attractant into the air surrounding the insect trapping device. Release rates of chemical attractants from lures may be and typically are proportional to temperature, i.e., increased release rate can be achieved with increasing environmental temperatures. Such release rates can also be related to flow rates of a gas past the attractant as well as the geometry and exposed surface area of the chemical attractant. These factors may be adjusted to supply the desired release characteristics for a given chemical attractant and given environmental conditions. As mentioned above, the temperature of a $CO_2$ containing exhaust plume or other carrier gas can be adjusted as needed to enhance attractant release from a trapping device under a given environmental condition.

The release of chemical attractants from liquid, semiliquid (including gels) and solid lures may be controlled to achieve an effective level of insect attraction over a period of several days to several weeks. According to an embodiment of the invention, attractant release rates for lactic acid may be controlled within a range of from about 1 mg/hr to about 30 mg/hr, such as, for example, about 2 mg/hr, about 3 mg/hr, about 4 mg/hr, about 6 mg/hr, about 8 mg/hr, about 10 mg/hr, about 12 mg/hr, about 14 mg/hr, about. 15 mg/hr, about 16 mg/hr, about 18 mg/hr, about 20 mg/hr, with the understanding that these values are merely representative and that "whole" number values in the given units are not required (the same applies throughout this specification, whenever numerical values are provided, unless the context indicates otherwise). These and other release rates according to different embodiments of the invention described herein may represent average release rates which are averaged over time periods of 1 hr., 6 hr., 12 hr., 24 hr., 5 days, 7 days, 10 days, 12 days, 14 days, 15 days, 18 days, 21 days, or other time periods.

Ammonia gas release rates may, depending on the particular source and its configuration, generally be higher than the release rate of lactic acid. Accordingly, in embodiments of the invention, the ammonia source and lactic acid source are designed to provide a mixture of both attractants effective to simulate bodily exudate and effective for capture of the target flying insects over an extended period of time, such as, for example, at least about two weeks, or at least about three weeks, or longer. For example, when the source of ammonia gas is ammonium bicarbonate, decomposition into ammonia, carbon dioxide and water generally starts at about 30° C. (86° F.) and will be rapidly decomposed at temperatures of about 60° C. (140° F.) or higher. When used at approximately these temperatures, release rates (based on the total of the chemical attractants) may be obtained over one, two, three or more weeks of use at levels ranging from about 16 mg/hr to about 130 mg/hr, or may be lower or higher, depending on the particular set of use conditions. For example, in an embodiment of the invention preferably for outdoor use, the release rate resulting from the decomposition of ammonium bicarbonate ranges on average over a one-two week period from about 50 to about 70 mg/hr after a briefly higher initial rate of release. In an embodiment of the invention directed to indoor use, the release rate resulting from decomposition of ammonium bicarbonate preferably ranges from about 1 mg/hr. to about 60 mg/hr. or, more preferably from about 5 mg/hr. to about 50 mg/hr. A release rate within the ranges indicated herein for the lactic acid and ammonia (from e.g., ammonium bicarbonate) provides for a sufficient longevity of the lure, usually at least about 2 weeks, such as at least about 3 weeks or longer, with effective simulation of exudate, such as sweat, effective for the capture of the target flying insects. In embodiments of the invention suitable for indoor use, the release rates of lactic acid and ammonia are preferably selected such that concentrations of ammonia and lactic acid are tolerable to human beings and more preferably within standards set for health, safety, or aesthetic purposes.

The amount of chemical attractant employed may be varied depending upon the size and shape of the lure, the formulations selected, and environmental conditions anticipated for the lure.

Release rates may be tailored to effectively trap a particular species of flying insect with a particular chemical lure. Some attractants, which are highly volatile, may use a lure in a geometric shape designed to reduce volatilization of the compound to preclude premature loss of lure efficacy. In contrast, other relatively inert chemical attractants may need heat or other reactions to promote dispersal into an air or $CO_2$ stream. Compounds exhibiting essentially no volatility are more difficult to control in terms of achieving efficacious insect attraction.

More generally, the release rates of lactic acid and ammonia (which may also include other attractant gases, including carbon dioxide and water vapor, such as in the decomposition of ammonium bicarbonate), into an outflow gas comprising carbon dioxide can generally be controlled to form mixtures in the outflow gas which mimic exudate, such as, for example, sweat or other bodily fluid of a human or other mammal, for an extended period of time, usually at least about two weeks, or at least about three weeks, or longer, for a continuous flow of the outflow gas. Of course, the longevity and effectiveness of the lure may be extended even further if the individual components of the lure are only intermittently contacted with the outflow gas. Additionally, release of chemical attractants can be achieved through diffusion or other passive means of air movement with respect to the chemical attractant or a gas stream may be directed to contact and move past the chemical attractant through use of fans, exhaust gas plume or other means.

Accordingly, in one embodiment the invention provides a lure for attracting flying insects comprising a source of lactic acid and a source of ammonia optionally combined with a gas stream. The gas stream may provide an approximately steady flow of air at flow rates between 10 L/min. to about 250 L/min., more preferably between about 40 L/min. to about 140 L/min. It should be understood that other flow rates may be selected to achieve the desired release rate characteristics for a given chemical attractant and given environmental conditions of use. The lure, when contacted with a steady flow of air optimally comprising an elevated level of carbon dioxide gas (for example, about 5 ml/liter) at a (flow rate of about 150 ml per minute and a) temperature of about 90° F., will release from attractant within the range of about 16 mg/hr to about 130 mg/hr of chemical attractant comprising ammonia from the ammonia source and will release attractant within the range of about 2 mg/hr to about 20 mg/hr of chemical attractant comprising lactic acid from the lactic acid source, for a period of at least about two weeks (e.g., at least about 300 hours), or at least about three weeks (e.g., at least about 500 hours).

The housings selected to hold solid and liquid chemical lures may be chosen to match a particular chemical lure with optimal exposure to air or gas stream, such as a $CO_2$ containing exhaust stream. As used herein $CO_2$ gas stream, $CO_2$ gas, $CO_2$ exhaust stream and the like refer to gases containing elevated levels of $CO_2$ with respect to ambient air and may include combustion exhaust gases, $CO_2$, and mixtures therein with air and other gases. Such housings may have multiple apertures that may be adjustable, thereby providing relatively fine control of the rate of attractant dispersal. For example, lures may be selected and configured to release a certain chemical attractant or mixture of attractants at a particular rate or rates, to attract a particular species of flying insect, e.g., disease carrying, biting or stinging, insect, as well as or in addition to extending the useful life of the lure. According to one embodiment of the invention the housing is arranged and configured to resemble a tubular basket, having one or a plurality of release vents. The housing basket may have an end cap. Lure housings according to an embodiment of the invention are configured to enable release of the attractants at a desired rate, such as, for example, about 2 mg/hr to about 20 mg/hr or any intermediate value within this range or higher value depending on the particular chemical attractant and target insect. According to one embodiment of the invention the release rate may be controlled at least in part by the exhaust gas flow rate and/or exhaust gas temperature, to which the chemical lure is subjected. The release rate may also, in some embodiments of the invention, be controlled by the area of the opening(s) of the housing for the chemical attractant or attractants. In an embodiment of the invention, the opening(s) or hole(s) may be variable in size. In another embodiment the opening(s) or hole(s) may be fixed in size. The shape of the openings or holes is not particularly critical and may be round, square, rectangular or any other regular or irregular geometric shape.

In one embodiment of the present invention, one or more of the chemical lures are formulated with suitable biodegradable polymers and are molded into articles assuming particular three-dimensional geometric shapes. Suitable biodegradable polymers are selected, for, inter alia, suitability for cast or extrusion molding. Such biodegradable polymers may decompose by random hydrolysis over time. As the molded biodegradable polymer erodes, fresh chemical attractant is continuously released from the molded article. The chemical lures can be selected such that complete degradation and erosion results in the production of more environmentally desirable compounds for easy disposal. For example, biodegradable polymers of poly (L(+)-lactide), polyglycolide and poly(lactide-co-glycolide) degrade to form L(+)-lactic acid, glycolic acid, and L(+)-lactic acid and glycolic acid, respectively.

The degradation rate can be varied from at least several weeks to several months or more, depending upon, for example, the amount of lure surface area exposed to air flow. The air flow may be selected based on the nature of the chemical compound and the intended environment of use for the lure. Degradation rates may also be controlled by changing the polymer or copolymer composition employed and/or by adjusting the geometric shape of the lure to increase or decrease surface area exposure to a $CO_2$ or similar gas or air stream. In general, amorphous (co)polymers degrade faster than semi-crystalline polymers.

In another embodiment of the invention, at least one chemical lure is prepared via simultaneous injection molding of at least one chemical attractant with a suitable polymer to form a molded article infused with attractant. Such baited, molded articles may be shaped to provide the maximal surface area necessary to ensure release of the chemical attractant over time. In another embodiment of the invention, the injection molding process comprises the introduction of a gas, thereby creating a matrix of holes within the molded article. These holes permit the flow of a gas stream, such as a $CO_2$ exhaust stream in conjunction with water vapor, through the molded article, thereby enhancing the release of the chemical lure contained therein. Such a design permits a relatively weak insect attractant to be released from the lure at a continuous rate to enable a functional level of the attractant to be dispersed over an extended period of time.

Injection molding of the chemical lure also permits the lure to be produced with integral parts providing a mechanical interface between the lure and the housing containing the lure. Such mechanical interfaces, such as hooks, lugs, snap fittings and the like, provide for lures tailored to fit particular housings. Such housings may be designated for use in a given market or with a specific trapping apparatus. In this manner, lures may be specifically designed for the environmental conditions and flying insect species associated with a particular geographic region. These market-specific chemical lures would be useful in providing end users with choices for tailoring their insect traps to evolving needs after purchase.

In another embodiment of the invention, chemical lures are attachable to insect trapping devices configured for use with a fuel supply containing combustible fuel for the generation of $CO_2$. In one embodiment of the invention an insect trapping device comprises a supporting frame; an insect trap chamber carried on the supporting frame; a combustion device carried on the supporting frame, and an insect lure positioned and configured to chemically attract insects toward the insect trap chamber. The combustion device comprises an inlet port for connection with the fuel supply, an exhaust port, and a combustion chamber communicating the inlet port with the exhaust port. The inlet port enables the fuel from the fuel supply to flow into the combustion chamber for continuous combustion therein to create an exhaust gas within the combustion chamber.

In an embodiment of the invention, the combustion device further comprises a catalyst element disposed within the combustion chamber downstream of a point at which the continuous combustion occurs. The catalyst body includes a catalytically active material that, during operation, converts carbon monoxide in the exhaust gas to $CO_2$. The combination of $CO_2$ exhaust gas and chemical attractant mimic the compounds released by mammals that flying insects detect in searching for hosts. Such features are described in co-pending U.S. patent application Ser. No. 10/264,260, the contents of which are incorporated herein in their entirety.

An exhaust outlet is carried on the frame and is communicated with the exhaust port of the combustion device. The exhaust port allows the exhaust gas to flow outwardly through the exhaust outlet so that insects attracted to the $CO_2$ in the exhaust gas will fly towards the exhaust outlet. An insect inlet is also carried on the frame adjacent the exhaust outlet. The insect inlet is communicated with the insect trap chamber to enable flying insects to enter the trap chamber through the insect inlet. A vacuum device communicated to the insect inlet is constructed and arranged to draw insects attracted to the exhaust outlet through the insect inlet and into the insect trap chamber. To enhance the attraction of insects to the insect inlet, a container comprising at least one chemical lure is attached to the insect trapping device at or near the insect inlet.

An embodiment of the invention includes a catalyst body for producing insect attracting $CO_2$, and the chemical lure or lures positioned and configured to provide a continuous supply of attractant at a controlled rate of release. Such arrangements may provide additional attraction to flying insects, as the insects are less likely to target the plume of $CO_2$ emanating from the exhaust outlet without flying near enough to the insect inlet to be drawn into the insect inlet for capture in the insect trap chamber. The inclusion of at least one chemical lure according to the embodiments of the present invention may substantially increase the effectiveness of the device in trapping insects attracted thereto, achieving a level of synergy that is not expected a priori.

Embodiments of the present invention described herein may utilize the chemical attractant alone or in combination with one or more additional materials which are able to attract flying insects. Thus, combinations of two or more insect attracting components may be employed, such as $CO_2$ together with at least one chemical lure, and/or one or more visual insect lures.

According to an embodiment of the invention, an attractant system for attracting flying insects comprises at least a first chemical attractant and at least a second chemical attractant, the first and second-attractants and/or the diffusion-products thereof, being chemically reactive with each other, wherein the first and second chemical attractants are stored to prevent contact between the first and second chemical attractants and/or between the diffusion products thereof.

The first chemical attractant may comprise a source of lactic acid such as in any of the embodiments described above. The second chemical attractant comprises a source of ammonia gas. These two, and optionally, one or more additional chemical lures and/or visual lures, may be arranged in a housing which, when contacted with a source of $CO_2$ gas, as previously described, will activate and cause diffusion of the individual attractants, e.g., lactic acid and ammonia, into the flow of $CO_2$ gas, such that the mixture of attractants commingle and form a combined chemical attractant which may be more efficient in attracting flying insects than any of the attractants alone.

To prevent premature dispersal of or interaction (including chemical reaction) between the first and second chemical attractants, the attractants may be separately packaged or sealed or packaged in a unitary housing, with the attractants being physically isolated from each other, such as, by example, hermetic sealing of the entire housing or of only the inlet and exhaust outlets thereof.

As used herein, the term "unitary housing" or "unitary package" or similar term, is intended to refer to any packaging which may be sold as a unit to an end use customer. In one embodiment of the invention, the unitary package is in the form of a housing with a first chamber and a second chamber, a first attractant being stored within the first chamber and a second attractant being stored within the second chamber. In one embodiment, the second chamber is housed within the same housing as the first chamber. The attractants and/or the housing and/or the chambers may have a substantially cylindrical shape. In one embodiment of the invention the walls of the housing define the walls of the first and second chambers with the same or slightly larger diameter than that of the attractants.

In another embodiment the first and second chambers are arranged internally within and spaced apart from the walls of the housing. For example, the internal walls of the housing may include two or more opposed projections defining a space within which the attractants may be more or less securely held in spaced apart relationship with the internal walls of the housing. For example, projections may be located at several longitudinally spaced apart locations along the length of the housing with the projections at each or some of the spaced apart locations being diametrically opposed (e.g., spaced at approximately 180°) or spaced apart by about 45°, 60° or 90° or any other convenient arrangement for securing the attractants within the housing. The space between the walls of the housing and the attractants may provide a flow pathway for a $CO_2$ gas stream or other gas stream capable of causing the respective attractants to diffuse into the gas stream for flow into the ambient environment for the attraction of, and subsequent capture or killing of, flying insects. The walls of the housing may also include one or more openings to further provide access to the attractants by the external flowing $CO_2$ or other gas stream. The one or more openings may be of the same or different dimensions and may be fixed or of variable size.

According to embodiments of the present invention, wherein the first and second chemical attractants are reactive with each other and/or where the volatile or diffusion products thereof are reactive with each other, any openings or passages allowing contact between the first and second attractants and/or between the vapors therefrom, will be sealed prior to the initial use so as to prevent such premature reaction and prolong the useful life of the lure.

In still another alternative embodiment of the invention, the first and second chemical attractants are part of an attractant system for mounting to an insect trapping apparatus, wherein the attractant system includes a housing defining at least a first chamber; at least a second chamber; the housing being constructed to be mounted to the insect trapping apparatus. A first chemical attractant is carried in the first chamber and a second chemical attractant is carried in the second chamber. The first and second chambers each have at least one opening for enabling the first and second insect attractants to diffuse therethrough, respectively. The first and second chambers are essentially isolated from one another by structure including one or more removable seals closing the openings of the chambers to essentially prevent intermingling or contact between the insect attractants and the diffusion products thereof (e.g., ammonia gas). Removal of the one or more removable seals opens at least one opening of the chambers, thereby allowing the insect attractants to diffuse therefrom so as to attract insects to the insect trapping apparatus when the housing is mounted thereto. In one embodiment of such attractant system, the housing defining the first chamber also defines the second chamber, further including structure for separating the first and second chambers so that otherwise chemically reactive attractants do not come into direct contact with each other in the common or unitary housing. An attractant system according to this embodiment of the invention is disclosed in further detail in the commonly assigned, copending provisional application, titled, "ATTRACTANT SYSTEM FOR MOUNTING TO AN INSECT TRAPPING APPARATUS," filed concurrently on Jun. 8, 2004, the entire disclosure of which is incorporated herein by reference thereto.

In any of the various embodiments of the invention, the housing will generally include at least one inlet by which a warm gas stream, such as $CO_2$ gas, may enter into contact with at least a portion of the exposed surface of the first and second attractants and at least one outlet associated with each chamber by which the $CO_2$ gas may exit the respective chambers and housing, together with the first and/or second attractants (e.g., lactic acid and ammonia) which have diffused from the attractants as a result of the contact with the flowing warm gas stream. Of course, the inlet(s) and outlet(s) for the flow of gas may be the same. The order in which the first and second attractants are loaded within the housing and/or contacted by the flowing gas stream, is arbitrary and may be in any order.

In another embodiment of the invention, the first and second attractants may be arranged in side by side relationship, e.g., with their respective longitudinal axes at least substantially in parallel and packaged in a common or unitary package or receptacle which prevents the premature contact between the otherwise reactive lures prior to the initial use.

In still another embodiment of the invention, the first and second chemical attractants may be arranged in an annular configuration so long as the flowing gas stream into which the chemical attractants are to be diffused can come into contact with each of the attractants. For example, the first attractant, with an external diameter $d_1$, may be fitted within a longitudinally extending opening or channel in the second attractant, wherein the opening or channel has a diameter $d_2$, where $d_2 \geq d_1$. In the case where $d_2 = d_1$, then the first attractant may include its own longitudinally extending opening forming a passageway for flow of the gaseous stream, while a separate flow of the gas stream in contact with the outer diameter of the second attractant, will provide for diffusion of each of the attractants from the first and second chemical attractants. In the case where $d_2 > d_1$, a gas stream flowing in the longitudinally extending opening of the second attractant will be in contact with surfaces of both attractants and, with optionally additional gas flow in contact with the outer surface of the second attractant, will provide for the diffusion of both attractants. Here again, the order of the first and second attractants as the interior or exterior attractants in the annular arrangement is arbitrary and may be reversed. This embodiment may be of particular interest for chemical attractants which are not chemically reactive or only slowly or not substantially chemically reactive under the anticipated storage conditions prior to use. For more reactive chemical attractants, a spacer and/or removable wrapper or other type of film or sealant can be used to maintain the lures out of direct contact.

The first and second chemical attractants may, in accordance with embodiments of the invention as described above, be maintained in physical isolation from each other until just prior to use. As used herein "physical isolation" or "physically isolated" means not directly touching or otherwise prevented from coming into contact under conditions which would allow the first and second attractants to react directly or for the gaseous and/or vaporous diffusion products thereof, such as, for example, ammonia and lactic acid, to react with each other. To this end, in one embodiment of the invention, either or both of the first and second attractants may be separately packaged or sealed, such as, for example, hermetically sealed, such as in a shrink wrap package.

In an embodiment of the invention, the lactic acid generating chemical attractant may comprise a polymeric gel comprising a gel network and lactic acid within but not chemically bonded to the gel network and may be contained within a plastic cartridge. The plastic cartridge, having at least one hole or other venting means in a side wall thereof for passage of lactic acid vapor, may itself then be fitted within a suitable receptacle having an open end. Either or both of the at least one hole or venting means of the cartridge and the receptacle may be temporarily sealed to prevent accidental contact of the lactic acid material contained therein or release of lactic acid therefrom. The source of ammonia gas as the second attractant may also be contained within its own cartridge or within a separate chamber of the cartridge housing the lactic acid containing gel. The ammonia source may be in the form of loose powder or granules contained within a porous bag or container and temporarily sealed with, for example, plastic or foil wrapping. Alternatively, the powder or granules may be molded or shaped into, for example, a monolithic configuration, such as, a cylindrical form, and fitted into the open end of the cartridge or the receptacle.

In an embodiment of the invention a cartridge housing includes first and second chambers separated by a membrane, shelf or other separator from the same or different material than the material of the housing, in order to separate the first and second attractants contained in the respective first and second chambers. Any openings in the housing for ingress or egress of gas flow, as described herein, would be temporarily sealed until just prior to use, such as by a strippable sealing tape, which may also bear indicia with advertising, ingredient and/or instructions for use.

Any or all of these devices or any other means for maintaining the first and second attractants in physical separation may be adopted within the scope of the invention.

As an alternative to openings, holes or vents, the housing or separating structures may be formed from a porous material which allows escape of gases, especially, gases at atmospheric pressure. For example, the housings, cartridges, membranes, and the like may be formed of sintered metal, open-cell foamed plastic or other porous materials having sufficient structural integrity for the expected handling and use conditions. Here too, the porous material may be effectively sealed by a removable sealant, e.g., shrink wrapping, tape, etc., to prevent leakage of any vapors which may be generated during storage.

Either the first or second attractant may be located in proximity, e.g., downstream, with respect to the $CO_2$ gas inlet.

In one embodiment of the invention, the source of ammonia gas is or comprises ammonium bicarbonate (also known as ammonium hydrogen carbonate) having the formula $NH_4HCO_3$.

The ammonium bicarbonate may be mixed with inert ingredients, including, for example, a binder to form granules. The granules may then be compacted into a desired shape depending on the housing and equipment with which it is intended to be used. In one embodiment the shape of the ammonium bicarbonate attractant may be substantially the same as the shape of the first attractant comprising lactic acid, for example, both may be substantially cylindrical.

Passing a stream of air or carbon dioxide gas over or through the ammonium bicarbonate will result in the generation of gaseous ammonia and carbon dioxide and water, the rate of production depending on the rate of flow of the air or $CO_2$ gas stream, the temperature of the gas stream and the exposed surface area.

In one embodiment of the invention, the second chemical attractant comprises a compacted or molded mixture of granules of ammonium bicarbonate, binder and water. In one embodiment, the amount of ammonium bicarbonate is from about 50% to about 90%, such as, for example, about 50%, about 55%, about 60%, about 65%, about 70%, about 75%, about 80%, about 85% or about 90%; the amount of binder is from about 5% to about 35%, such as about 5%, about 10%, about 15%, about 20%, about 25%, about 30%, or about 35%; and the amount of water is from about 3% to about 20%, such as, about 3%, about 5%, about 10%, about 15%, about 20%, all based on the total weight of the mixture.

Any suitable, usually inert, binder may be used. Examples of suitable binders include, for example, starch, wax (e.g., Carnauba wax, beeswax), low-molecular weight, water-soluble polymers (e.g., polyvinyl alcohol, poly(ethylene glycols)), cellulose and cellulose derivatives (e.g., microcrystalline cellulose, modified cellulose, cellulose ethers, such as alkyl celluloses), gums (e.g., guar gum, tragacanth gum), fatty acids and esters (e.g., stearic acid, alkylstearates), dibasic calcium phosphate, mannitol, fructose, xylitol, and the like, as well known to those skilled in the art. Water also provides a binding function.

Ammonia gas may also be generated by the reaction between an ammonium salt with a base. The ammonium salt and the base may be provided as a homogeneous or intimate mixture of solid finely divided particles of each reactant. Application of moderate heat, which may be provided from, for example, the flow of $CO_2$ gas, or from other external source, will initiate the reaction. Here, the reaction product will include the ammonia gas and by-product water vapor. The ammonium salt may be an inorganic ammonium salt or an organic ammonium salt. As examples of inorganic salts, mention may be made of the halide, sulfate, sulfide, nitrate, and phosphate salts. Ammonium acetate is representative of organic ammonium salts. Other carboxylic acids may also be used. Representative examples of the bases which may be used include such strong bases as the hydroxides of alkali metals (e.g., sodium, potassium, lithium); alkaline earth metals (e.g., calcium); oxides (e.g., calcium oxide); carbonates (e.g., calcium carbonate).

Often, in view of economic considerations, selection of ammonium chloride as the ammonium salt and the bases calcium oxide (lime), calcium hydroxide (slaked lime) or calcium carbonate (limestone) may be convenient. It should be noted that when calcium carbonate is selected, ammonium carbonate is formed as an intermediate, which is generally present as a mixture of ammonium bicarbonate and ammonium carbamate in a roughly 2:1 ratio. As discussed above, ammonium bicarbonate will decompose to ammonia when contacted with, For example, the warm flow of $CO_2$ gas. The carbamate, upon-contact with air or $CO_2$ gas, will also be converted to the bicarbonate and, therefore, be able to generate additional ammonia gas.

Any liquid or solid inorganic or organic ammonium compound which upon decomposition will release ammonia gas may also be used. Examples of suitable ammonium compounds include, for example, ammonium acetate, ammonium benzoate, ammonium carbonate, ammonium carbonate/scandium carbonate double salt monohydrate, ammonium chloride, ammonium citrate, ammonium disodium amminepentacyanoferrate (II) hydrate, ammonium ferrocyanides (II) hydrate, ammonium formate, ammonium hydroxide (ammoniated water), ammonium hydrogencitrate, ammonium hydrogenphosphate, ammonium hydrogen sulfate, ammonium iron(III) citrate, ammonium lactate, ammonium nickel (II) sulfate hexahydrate, ammonium niobium oxalate, ammonium nitrate, ammonium nitrate matrix modifier solution, ammonium oxalate monohydrate, ammonium perchlorate, ammonium persulfate, ammonium sulfamate, ammonium sulfate, ammonium sulfide water solution, ammonium sulfide monohydrate, and ammonium L-tartrate.

It is also within the scope of the invention to use ammonia gas itself, e.g., pressurized ammonia cylinders or ammonia solution in suitable solvents.

The selection of the ammonium compound or ammonia gas may depend on the availability in the locale where the lure is intended to be used. In embodiments of the invention, wherein the lure is expected to be or specifically designed for use within an enclosed space, such as the user's home, or otherwise where the fumes or vapors are expected to come into contact with humans or other animals, it is especially important that the chemical lures, including decomposition products, are non-toxic and non-irritating and generally safe. In an embodiment of the invention food grade lactic acid and food grade ammonium bicarbonate are used as the chemical attractants. However, any comparable attractants generally recognized as safe for consumption and/or contact with humans and other animals, may be used.

In another embodiment of the invention visual lures may be employed to synergistically enhance the attraction of a trapping device to flying insects. For example, visual insect lures may be selected to provide visual cues tailored to attract particular species of flying insects. Such visual lures may be configured to provide at least two relatively large contrasting colored fields. The visual lures may comprise one or more of a shiny black surface, a high gloss mirrored silver surface, or fields of magenta and silver. Visual lures may comprise a magenta:silver field in the ratio of about 50:50 to about 70:30. The ratio of magenta:silver may be from about 60:40 to about 70:30.

The visual lure may be fashioned in a geometric shape attached to a trapping device. The geometric shape may be selected to specifically attract particular flying insect species. For example, the visual lure may comprise a combination of curvature and plane features. Colored spheres and cones have demonstrated attractiveness to certain flying insects. However, many shapes may be designed to maximize surface area for exposure of color attractants to insects, thereby enticing susceptible flying insects to a trapping device.

Visual lures may also be integrated into the functional or structural features of a trapping device. Thus, a visual insect lure may comprise at least part of one or more colored insect trap components, such as stand legs, a trap unit housing, an exhaust outlet nozzle and an insect intake nozzle. For example, a trapping device may comprise an insect intake nozzle molded to have a magenta portion and a silver portion, a color scheme that has, surprisingly, demonstrated superior insect attracting capabilities. Such an intake nozzle, in combination with one or more chemical lures and a $CO_2$ exhaust plume, may provide a flying insect trapping device capable of exceptionally high insect capture counts.

A water-based gelatinous form of lactic acid in accordance with an embodiment of the present invention is prepared from a food-grade L(+)-lactic acid aqueous solution. In an embodiment of the invention, the product is formulated to be able to release L(+)-lactic acid at relatively high rates for at least about 3 to 4 weeks in Mosquito Magnet® (a trademark of American Biophysics Corp., Rhode Island, U.S.) traps.

The gel product may be formed by mixing L(+)-lactic acid solution with a UV-curable aqueous solution whereby the whole solution forms a gelling network (L(+)-lactic acid gel) under ultraviolet (UV) radiation. There is no chemical connection between the L(+)-lactic acid and the formed gelling structure. In other words, there is no chemical bond between the L(+)-lactic acid and the gelling network. Therefore, L(+)-lactic acid can be released freely from the L(+)-lactic acid gel at desired rates depending on, for example, the environmental temperature, the surface area of the chemical attractant which is exposed to the environment, and the like.

In one embodiment of the invention the L(+)-lactic acid gel may be inserted or formed in a cartridge.

In an embodiment of the invention a water-gel layer may be placed under the L(+)-lactic acid gel, to provide a water reservoir that supplies water to the L(+)-lactic acid gel continuously in order to maintain required release rates and time.

Table 1 shows representatives chemicals which may be used in the manufacture of a lactic acid gel according to various embodiments of the invention.

TABLE 1

| Chemical Name | Commercial Name or Trade Name | Function | Manufacturer |
|---|---|---|---|
| L(+)-lactic acid aqueous solution (88 wt %); | Purac ® FCC 88 | Mosquito attractant | PURAC America, Inc. |
| L(+)-lactic acid aqueous solution (80 wt %) | Purac ® Salanic | | |
| Polyethylene Glycol 600 Diacrylate (100%) | SR 610, Acrylic Ester | Cross-linking agent | Sartomer Company, Inc. |
| 2,2-Dimethoxy-1,2-diphenylethan-1-one (100%) | Irgacure ® 651 (Ciba ®) | Photo-initiator | Ciba Specialty Chemicals Corp. |
| Phosphine oxide (50%) | Ciba ® Irgacure ® 819 DW | Photo-initiator | Ciba Specialty Chemicals Corp. |
| Water, distilled | | Diluent | Culligan Water |
| Acrylic acid (99%) | | Reactant to make sodium acrylate | Aldrich Chemical Co., Inc. |
| Sodium hydroxide, 3 mm Flakes, (98%) | | Reactant to make sodium acrylate | Aldrich Chemical Co., Inc. |

Individual cartridges containing the above lactic acid gel formulation may be prepared by mixing ingredients from Table 1 in a plastic container, e.g., high density polyethylene, polypropylene, polyethylene terephthalate or other inert plastic) with stirring in the following order: SR 610, Irgacure 651/acetone solution, lactic acid solution and water.

A solution of the Irgacure 651 in the acetone is first prepared and the resulting solution should be stored in a dark, e.g., amber sealed container until ready for use. The weight ratio of photoinitiator to acetone may range from about 5 to about 25%, or from about 10 to about 20%.

In one embodiment of the invention clear PET (polyethylene terephthalate) film is used to make a cartridge in a vacuum-forming and heat-sealing process. The cartridge can release L(+)-lactic acid at certain rates through the hole/holes on the top surface of the cartridge. The size and the number of the holes control the release rate of L(+)-lactic acid from the cartridge. In one embodiment of the present invention, there is one hole on the surface of the cartridge; the size of the hole is about 0.14-inch in diameter. A multi-layer tape, e.g., composed of aluminum foil and heat-sealable plastic film, may be to seal the release surface of the cartridge. The seal may also be used as a label for the cartridge.

In one embodiment a solution of sodium acrylate is first prepared. Sodium acrylate is an example of a UV-curable aqueous solution and an aqueous solution of sodium acrylate and lactic acid forms a gelatinous structure when reacting with a di-or tri-functional cross-linking agent such as SR 610 (which is an example of a di-functional cross-linking agent with two double bonds in the molecule providing functional groups) under heat or UV-radiation. Sodium acrylate can be prepared by the reaction of sodium hydroxide and acrylic acid, both easily obtainable from a wide variety of manufacturers. Alternatively, commercially-produced sodium acrylate can be used instead of in situ formation.

A UV-curing system (e.g., Fusion F300S-6 made by Fusion UV Systems, Inc, which includes a UV lamp and a conveyor), may be used to effect UV curing.

A sodium acrylate solution (35.5 wt % in distilled water) may be prepared using the ingredients and proportions shown in Table 2. The completion of the reaction may be determined by controlling the amount of reactants and the change in pH value of the reacting solution. The pH of a freshly-prepared sodium acrylate water solution (35.5 wt %) is between 8 and 9 (determined using pH paper). Since both sodium hydroxide and acrylic acid are strongly corrosive and the reaction is highly exothermic, the reaction may be performed in a cold-water bath. However, any method for the manufacture of sodium acrylate is within the scope of the present invention. Furthermore, it is also evident that sodium acrylate from a commercially available source may be used.

TABLE 2

| Chemical | Reference weight (g) | Weight % |
|---|---|---|
| Sodium hydroxide | 40.0 | 15.1 |
| Distilled water | 153.0 | 57.7 |
| Acrylic acid | 72.0 | 27.2 |
| Total | 265.0 | 100.0 |

The sodium hydroxide flakes (40.0 g) are dissolved in distilled water (153.0 g) to make a sodium hydroxide solution and then added gradually to acrylic acid (72.0 g) with stirring. The pH of the final solution may be determined with a pH meter. Sodium acrylate (94.0 g) is formed in the final solution with a concentration of 35.5% by weight.

In one embodiment of the invention the lactic acid gel lure has a two-phase structure that includes the L(+)-lactic acid gel (e.g., on the top of the cartridge) and a water-gel (e.g., on the bottom of the cartridge). Suitable compositions of the L(+)-lactic acid gel and water-gel are shown in Table 3. In order to prepare the L(+)-lactic acid gel and the water-gel, the sodium acrylate solution is first stirred in a container to which water (if needed), L(+)-lactic acid, SR 610, and Irgacure 651 are added in that order. It is well understood, by one skilled in the art, that different amounts and procedures for creating similar L(+)-lactic acid gels and water-gels are possible.

TABLE 3

| Chemical | Water-gel (wt %) | L(+)-lactic acid gel (wt %) |
|---|---|---|
| Sodium acrylate solution (35.5 wt %) | 47.0 | 37.0 |
| L(+)-lactic acid (Purac ® FCC 88) | 3.4 | 59.6 |
| SR 610 | 3.4 | 2.4 |
| Irgacure 651 solution | 1.2 | 1.0 |
| Distilled water | 45.0 | |
| Total | 100.0 | 100.0 |

The amount of the L(+)-lactic acid gel and the water-gel in a cartridge may be selected to provide the highest release rate and useful life. In one embodiment, 11 g of L(+)-lactic acid gel and 3.5 g of water-gel showed a release rate higher than 10 mg/hr for 14 days and a release rate of 4 mg/hr to 9 mg/hr for additional 6 days (at about 90° F.). Increasing the amount of the water-gel could lead to a release rate higher than 10 mg/hr for longer than 3 weeks.

The lactic acid solution may be gelled, (and the water-gel solution when used) by adding the ingredients directly to a plastic cartridge and passing the cartridge under a UV or heat source. In a one embodiment, a UV lamp with a D-Bulb for UV-A and UV-V radiation is used. In another embodiment, the cartridges are passed under the UV or heat source on a conveyor at a speed of about 10 ft/min. If both the lactic acid gel forming solution and the water gel forming solution are both used, water-gel is first formed and the L(+)-lactic acid gel solution is dispensed on top of the water-gel in the cartridge and then cured. Heat-sealable tape may be applied to any of the openings on the surface of the cartridge or each cartridge and packaged in a gas impermeable wrapper for shipping to customers. It is within the scope of this invention that the L(+)-lactic acid gel solution be cured before or during the curing of the water-gel solution. It is also within the scope of this invention that the L(+)-lactic acid gel solution and water-gel solution be cured separately and optionally assembled at a subsequent step.

The liquid L(+)-lactic acid and water are trapped in, but as mentioned earlier not combined with, the gelling network.

In another embodiment of the invention, the gel-forming curing reaction is carried out with only a curable polyunsaturated compound, e.g., without a photo-curable, monounsaturated compound such as sodium acrylate. In this case, for example, the polyunsaturated component will provide sufficient free radicals to form a three-dimensional network appearing as a gelatinous structure with entrapped lactic acid solution. The lactic acid solution may contain sufficient water such that a separate water-gel layer may not be required. In yet another embodiment of the invention, a lure is provided with a source of lactic acid with or without a source of ammonia wherein the source of lactic acid comprises an aqueous solution of lactic acid in a polymeric gel that is substantially free of acrylate moieties where substantially free of acrylate moieties means the polymer used in preparation of the gel network either has no acrylate moieties or has only acrylate moieties at some or all of the termini of polymers such that the acrylate moieties are useful for cross-linking such polymers in forming the polymeric gel. An advantage of such an embodiment in comparison with polymeric gels formed from acrylate monomers or polymers containing substantial amounts of acrylate moieties is that the amount of acrylate moiety is reduced in the lure and thereby reduces the repellant effect of certain acrylate moieties and byproducts thereof.

For example, ingredients shown in the following Table 4 may be used to prepare a lactic acid-containing gel chemical attractant lure according to an embodiment of the present invention.

TABLE 4

| Ingredient | Wt % | Weight (g) per Cartridge |
|---|---|---|
| Purac ® Sanilac (80% solution) | 44.21 | 6.10 |
| SR 610 | 15.00 | 2.07 |
| Irgacure 651 (18.2% in acetone) | 1.10 | 0.15 |
| Distilled Water | 39.69 | 5.48 |
| Total | 100.00 | 13.80 |

The procedure for preparing the gel from the above formulation is substantially the same as described above. For example, the ingredients are added to a suitable container, e.g., a plastic cartridge, such as, for example, polyethylene or polypropylene) with stirring, in the order, SR 610, Irgacure 651 solution, lactic acid solution, and water. The resulting mixture is subject to UV curing in the cartridge. The cartridge may be heat-sealed to seal any openings in the cartridge.

The amount of the photoinitiator (about 0.2% in formula shown in the above Table 4) may be selected to achieve the desired level of dissociation of the double bonds of the polyunsaturated ingredient and, hence, the desired level of crosslinking and gellation. The manufacturer of Irgacure recommends, depending on the particular application, an amount of the "651" ranging from about 0.5 to about 6% by weight. However, it has been found that the lower amount (about 0.2%) used in this embodiment of the invention, nevertheless, induces a degree of crosslinking and gellation which results in a gel having a holding capacity which is able to at least substantially stably retain the lactic acid solution in the gel without leakage upon storage for several weeks to months. The liquid holding capacity of a gel may be readily determined by routine procedures including trial and error.

While the L(+)-lactic-acid gel and the water-gel, when used, are formed using a UV-active polymerizing molecule (acrylate), with the assistance of the free-radical forming curing photoinitiator, it is well understood by one of ordinary skill in the art that gels can be formed by other means. For example, gels can be formed by addition polymerization, condensation polymerization, carbocation polymerization, free-radical polymerization, anionic polymerization, and organometallic polymerization. The monomer used can also vary and includes substituted or unsubstituted alkanes, substituted or unsubstituted alkenes, substituted or unsubstituted alkynes, substituted or unsubstituted dienes, substituted or unsubstituted saccharides, substituted or unsubstituted nucleotides, substituted or unsubstituted lipids, and substituted or unsubstituted urethanes. The addition of groups such as; halo-, amino-, oxo-, hydroxyl-, thio-, nitro-, alkoxy-, an aryloxy- to many standard compounds can cause them to be suitable for polymerization reactions. Gel polymers may be natural (e.g., rubber latex) or synthetic (e.g., nylon and polyvinylchloride PVC). Gels may also be formed from other non-polymerization reactions, e.g., acid-base reactions, precipitation reactions, and substitution reactions.

In addition to UV-light, polymerization reactions can be initiated, controlled, and terminated by a number of means including heating, cooling, free radicals, visible light, infrared (IR) light, beta radiation, and gamma radiation.

Other forms of solid, semi-solid, or liquid lactic acid can also be used in accordance with the present invention. For example, sintered lactic acid can be used instead of, or in conjunction with, the lactic acid gel. It is also within the scope of this invention for the lure to comprise a gel form of lactic acid with a sintered form of another attractant or a sintered form of lactic acid with a gel form of another attractant.

The following is a representative example for the preparation of an ammonium bicarbonate as a chemical attractant for generating ammonia gas according to an embodiment of the invention.

The following formulation is prepared:

TABLE 5

| Ingredient | Amount (wt %) |
|---|---|
| Ammonium bicarbonate[1] | 75 |
| Starch[2] | 16.5 |
| Water, distilled | 8.5 |

[1]Available as "ammonium bicarbonate-treated" from Church & Dwight, Inc.
[2]Available as National ® 1215, from National Starch & Chemical Corp.

To prepare the above formulation, the ammonium bicarbonate powder and the starch powder are added to a mixer, in any order or simultaneously, and the water is slowly added with stirring at high speed to form loose wet granulates. The granulates are then fed into the barrel of a molding machine and molded into individual shaped products, such as, for example, cylindrical shapes.

In one embodiment of the invention, suitable for use together with a lactic acid gel product, such as described above, an individual shaped product may weigh from about 12 to about 50 grams and have a diameter of about 0.5 to about 1.5 inches and a length of from about 1.5 to about 3.5 inches.

FIG. 1 shows an example of an insect trapping apparatus, generally indicated at 10, with which the attractant system, generally indicated at 12, may be used. The apparatus 10 shown in FIG. 1 is the MOSQUITO MAGNET LIBERTY, which is described in U.S. Patent Appln. No. 2003/0084604 A1 filed Oct. 4, 2002. The attractant system 12 may also be used with any other type of insect trapping apparatus, such as other combustion based types, and non-combustion based types, such as the CDC light trap. For other patents/applications illustrating examples of such apparatuses, reference may be made to U.S. Pat. Nos. 6,286,249, 6,145,243, and U.S. patent application Ser. Nos. 10/445,245, filed May 27, 2003; Ser. No. 10/445,199, filed May 27, 2003; and Ser. No. 10/686,815, filed Oct. 17, 2003. Each of the patent applications mentioned above, or otherwise mentioned anywhere else in the present application, are hereby incorporated by reference into the present application in their entirety.

The trapping apparatus 10 includes a supporting frame 14 with a combustion device (not shown) mounted inside the frame 14. The combustion device connects to a propane tank (not shown) by a conventional regulator and functions to catalytically combust the propane to generate an exhaust gas. The exhaust gas has a high $CO_2$ content and contains moisture from the catalytic reaction. Further details concerning this operation are found in the aforementioned patents/applications. The exhaust gas flows outwardly from an outlet tube 16 defining a downwardly facing outlet opening 18. This allows a plume of the exhaust gas to flow downwardly from the outlet opening 18 and then spread out from the apparatus 10. Mosquitoes and other insects that are highly sensitive to $CO_2$ will be attracted to the plume and follow it to its source, namely the outlet opening 18.

The outlet tube 16 is mounted concentrically within an inlet tube 20 having a downwardly facing annular opening 22. The inlet tube 20 and the inlet opening 22 are communicated to an airflow generator in the form of a fan (not shown) mounted inside the frame 14. The fan draws an inflow in through the inlet opening 22 and the inlet tube 20. The inflow flows adjacent and counter to the outflow so as to draw the insects that are attracted to the outflow and flying towards the outflow opening 18 into the inlet opening 22 and the inlet tube 20. Typically, most insects will follow the upper edge of the outflow, so positioning the inflow so that it flows counter and adjacent to the upper edge of the outflow is advantageous for capturing those insects.

An insect trap chamber (not shown) is also mounted in the frame 14. The insect trap chamber may be either upstream or downstream of the fan, but in either case the fan causes the inflow to flow into the insect trap chamber. The insect trap chamber may have any construction, and in the illustrated apparatus 10 it is a mesh bag. As the inflow flows into the insect trap chamber, insects drawn in with the inflow are captured. Once captured, they can be left to die by dehydration/starvation, or poison may be used inside the insect trap chamber. Also, the trapping apparatus 10 could use an electrocution system for killing the insects. As another alternative, instead of killing the insects, the trapping apparatus 10 may be used for scientific study purposes with the insects being removed from the trapping apparatus 10 alive.

The attractant system 12 is designed to be mounted inside the outlet tube 16 of the apparatus 10. However, the system 12 may be configured to mount in the outlet tube of any other type of apparatus, or at any other location on any type of apparatus. Generally, the attractant system may have any construction or configuration, and the one illustrated herein is not intended to be limiting.

To accommodate receipt of the system 12, a receptacle 24 is mounted inside the outlet tube 16. For convenience, references made here to directions with respect to the attractant system 12 or the receptacle 24 are made with respect to the orientation in which they are installed in the apparatus 10.

The receptacle 24 may be provided as an original part of the apparatus 10, or it may be sold as a retrofit kit. The receptacle 24 is shown in FIGS. 3-7. The receptacle 24 is generally elongated with a closed and rounded upper end cap 26, and an annular ring 28 at its bottom end defining a downwardly facing opening 30. Four elongated members 32 extend longitudinally between the end cap 26 and the ring 28 to connect the same together, although any number of such members 32 may be used. These members 32 are generally parallel to one another and define a series of longitudinally extending apertures 34 therebetween. This construction defines an interior space with an open end (i.e., opening 30). The space has a cross-sectional configuration that is essentially consistent along the length of the receptacle 24 between ring 28 and end cap 26 (the cross-section being taken essentially perpendicular to the longitudinal direction of the receptacle 24).

The receptacle 24 also has a series of wings 36 extending outwardly from the members 32, and each of an opposing pair of the members 32 has a post 38 extending outwardly therefrom. The posts 38 have internal bores 40 and the outlet tube 16 of the apparatus 10 has a pair of diametrically opposed fastener receiving openings 42. To mount the receptacle 24 within the outlet tube 16, the receptacle 24 is inserted into the tube 16 to align the internal bores 40 of the posts 38 with the fastener receiving openings 42 of the tube 16. Fasteners, such as screws 44, are inserted through the openings 42 and into the bores 40 to secure the receptacle 24 within the tube 16. The wings 36 are configured so that they engage the inner surface of the outlet tube 16 to stabilize the receptacle 24 within the outlet tube 16. The wings 36 also create space between the main body of the receptacle 24 and the inner surface of the outlet tube 16 for allowing the outflow to flow around and past the receptacle 24. The invention, however, is not limited to this mounting arrangement, and any other suitable manner of mounting the receptacle 24 may be used.

In the illustrated embodiment, the receptacle 24 is molded integrally as a one-piece plastic part. This is preferred for cost savings reasons. However, the receptacle 24 may be made in any suitable manner, and may have any construction and configuration. The receptacle 24 illustrated is provided for illustrative purposes and is not intended to be limiting.

The ring 28 has an internal diameter that matches up with the external surfaces of the walls 32. A first diametrically opposed pair of the walls 32 extends for a small extent along the inner surface of the ring 28. The ring 28 has a pair of diametrically opposed tab receiving openings 46. These openings 46 are axially with and spaced from the ends of the first diametrically opposed pair of walls 32 mentioned above. A second diametrically opposed pair of the walls 32 extends along the entire axial length of the inner surface of the ring 28 and each defines a series of ridges 48 of their ends. The arrangement of these structures can be appreciated from FIGS. 4-7.

The attractant system 12 has an elongated generally cylindrical housing 50. The housing 50 has an upper end wall 52, a lower end wall 54, and a central wall 56. A first chamber 58 is defined between the upper end wall 52 and the central wall 56, and a second chamber 60 is defined between the central wall 56 and the lower end wall 54. A first diffusible insect attractant 62 is carried in the first chamber 58, and a second diffusible insect attractant 64 is carried in the second chamber.

The insect attractants 62, 64 may be of any type, and generally will be of the type that may chemically react with one another. In one embodiment, it is contemplated to use a lactic acid gel as the first insect attractant 62, and a powdered ammonium bicarbonate as the second insect attractant 64. Because lactic acid is an acid and ammonium bicarbonate is a base, these are examples of attractants that would react with one another, as acids and bases can react to form a salt. Any other diffusible liquid, solid, or semi-solid insect attractants may be used, and these examples should not be considered limiting. Although the chambers 58, 60 are shown as being axially adjacent one another, they could extend adjacent one another for the longitudinal length of the housing 50, or be arranged in any other manner. Reference may be made to U.S. patent application Ser. No. 10/431,586, the entirety of which is hereby incorporated into the present application by reference, for details on the lactic acid gel, for example.

The housing 50 has a plurality of openings therein to enable diffused insect attractant to flow out from the chambers 58, 60. The size, number and arrangement of the openings depend on the desired release rate for the attractants 62, 64 in the chambers 58, 60. Thus, the size, number and arrangement of the openings may vary, and the openings in the illustrated embodiment are not intended to be limiting.

The first chamber 58 has a pair of relatively large rectangular openings 66 extending axially on one pair of diametrically opposing sides of the chamber 58. The first chamber 58 also has a series of axially spaced, relatively small openings 68 on another pair of diametrically opposing sides of the chamber 58. The second chamber 60 has a single relatively small opening 70 spaced axially from the opening 68.

The external configuration of the housing 50 can best be appreciated from FIGS. 4-6 and 8. A series of ridges 72, four as illustrated, extend axially along the length of the housing 50, except where interrupted by openings. These ridges 72 define a corresponding series of grooves 74 therebetween that also extend axially along the length of the housing 50. The cross-section of the housing 50 (taken essentially perpendicular to its longitudinal direction) closely matches the cross-section of the interior space of the receptacle 24. This enables the system 12 to be mounted to the apparatus 10 by inserting the housing 50 longitudinally into the elongated interior space of the receptacle 24.

To mount the attractant system 12 to the receptacle 24, which is already mounted to the apparatus 10, the housing 50 is aligned axially with the opening 30 of the receptacle's ring 28 so that the housing's grooves 74 align axially with the receptacle's members 32 and the housing's ridges 72 align axially with the openings 34 defined between the members 32. The user then slides the housing 50 axially into the interior of the receptacle 24. When the housing 50 is fully inserted, the upper ends of the ridges 72 will abut against the lower edge of the end cap 26 to limit further axial movement.

Also, the lower end of the housing 50 has a pair of engaging tabs 76 carried on resiliently flexible arms 78. These tabs 76 are releasably received in the tab receiving openings 46 of the ring 28. The engagement of the tabs 76 within the openings 46 inhibits the housing 50 from sliding out of the receptacle 24, such as by gravity. To release the housing 50 from the receptacle 24, the arms 78 can be resiliently flexed inwardly to withdraw the tabs 76 from the openings 46. These arms 78 may be formed integrally as one-piece with the housing 50 or formed separately and attached thereto.

The housing 50 is manufactured by injection molding the housing 50 itself and the center wall 56 as one piece, with the ends of the housing 50 being open. Then the openings 66, 68, 70 are cut-out. Alternatively, the openings 66, 68, 70 may be formed as part of the injection molding operation. Next, the attractants 62, 64 are placed in the chambers 58, 60 and the molded plastic end walls 52, 54 are fixedly attached to the open upper and lower ends of the housing 50 to close the same.

To seal the chambers 58, 60 and prevent the insect attractants 62, 64 from diffusing and intermingling with one another prior to use of the attractant system 12, one or more removable seals are provided to close the openings 66, 68, 70. Closing the openings 66, 68, 70 essentially isolates the chambers 58, 60 from one another to essentially prevent intermingling of the attractants (and the wall 56 keeps them physically separated and isolated as well). The term "essentially" is used to acknowledge the fact that minor errors or inconsistencies in manufacturing or design may allow for a slight amount of attractant 62, 64 to escape through the one or more seals, any slight gaps between the center wall 56 and the housing 50, and/or any slight gaps between the end walls 52, 54 and the housing 50. Of course, it is preferred that there be no such escape of attractant, but it is understood that some slight amount may escape.

By preventing the attractants from co-mingling prior to usage, their longevity and effectiveness during usage are enhanced. Specifically, in a retail store setting, the attractant system 12 is first made by the manufacturer, then packaged for shipping and delivered to the retail store, typically via the retail store's distribution center. Then, the attractant system 12 will be placed on a shelf or display rack until purchased and used by a consumer. The time period between manufacturing of the attractant system 12 and its use by a consumer may be a few weeks and possibly over a month. If the attractants 62, 64 were allowed to intermingle with each other, they could become depleted by the time the user uses the system 12, thus reducing the period of time during which the attractants 62, 64 will function with a high level of efficiency. Thus, using one or more seals to close the openings 66, 68, 70 is desirable to prevent this intermingling from occurring. Also, using the wall 56 to keep the attractants 62, 64 physically separated during use minimizes any intermingling/reaction between the attractants 62, 64 within the housing 50.

Figure 11:
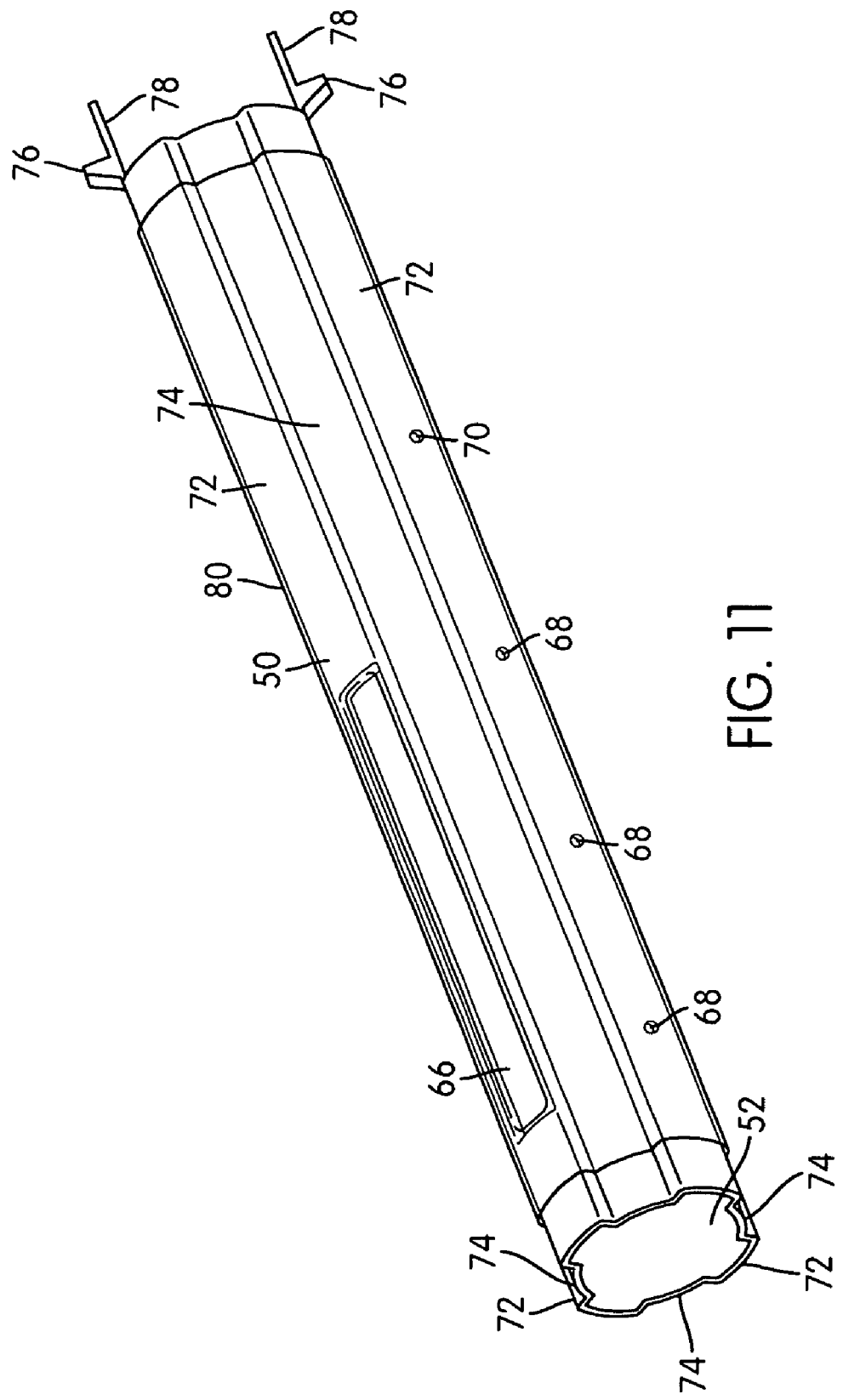
FIG. 11 is a perspective view of the attractant system with a plastic film heat shrunk thereon to seal its openings.

In the illustrated embodiment the one or more seals are constituted by a plastic film 80. This plastic film 80 encircles the housing 50 and is heat shrunk thereon to cover the openings 66, 68, 70 of the chambers 58, 60. This is done by placing a tube of the film 80 over the housing 50, with the tube having a slightly larger diameter than the housing 50. Then, heat is applied to shrink the tube and cause the film 80 to firmly encase the housing 50 and close off the openings 66, 68, 70. The preferred film 80 for this application may be any generally gas impermeable material which is inert to the chemical attractants and any diffusion products therefrom. The film 80 is seen in FIG. 11.

Other types of seal(s) may be used instead of film 78, for example, adhesive strips may be used to cover and close off the openings 66, 68, 70. Generally, any suitable type of seal(s) may be used to close off the openings 66, 68, 70 and the size, shape and structure of such seal(s) may vary. Likewise, a plastic film sheet may be wrapped tightly around the housing 50 and secured in place. Also, in some configurations, deformable plugs could be forced into the various openings to seal them off. The present invention is not limited to the examples mentioned herein.

Prior to using the system 12 in apparatus 10, the user will remove the film 80, or whatever other seal is being used. This will permit the insect attractants 62, 64 to diffuse out through openings 66, 68, 70 to facilitate attracting insects to the apparatus 10.

EXAMPLES 1-4

These examples illustrate embodiments of the invention wherein a combination lure includes a lactic acid-containing gel, as a first chemical attractant, in combination with ammonium bicarbonate (a source of ammonia) as a second chemical attractant.

The mosquito attractiveness of the combination was evaluated in Mosquito Magnet™ Liberty and Professional (Pro) traps manufactured by American Biophysics, Corp. A top-open carrier compartment (for holding attractant) was used, which allows the plume (carbon dioxide, water vapor) to pass through the surface of the attractant cartridges. The traps, in field tests, were rotated between test sites to reduce or eliminate the possible influence from conditions associated with the test sites in mosquito distribution, geography and other environmental factors.

Attractant Samples:

The combination according to an embodiment of the invention is a two-component attractant with food grade L(+)-lactic acid having a formulation as shown in Table 4 above and ammonium bicarbonate powder, either having the formulation as shown in Table 5 above as the active ingredients or as a directly compressed powder in a porous bag. The L(+)-lactic acid and ammonium bicarbonate lures are formulated individually and sealed in separate packages that are then physically combined together in one large package—such as that shown in FIG. 11. The L(+)-lactic acid part is a polymeric gel that was photo-cured in a plastic cartridge with multiple holes to allow release of L(+)-lactic acid in vapor form. The ammonium bicarbonate part is a pressure-molded solid in cylinder form sealed in a plastic cartridge with small holes for releasing ammonia, carbon dioxide and water vapor or is ammonium bicarbonate powder directly pressed and sealed in a bag made with porous polypropylene film.

The L(+)-lactic acid gel is placed in the first cartridge chamber in the side with an open space and the molded ammonium bicarbonate cylinder or ammonium carbonate powder in a porous bag is placed in the second chamber in the sealed side with a release hole covered with a piece of red tape. The two chambers are isolated to avoid an acid-base chemical reaction between the two active components in the package during storage and application.

EXAMPLE 1

This example demonstrates that the combination lure effectively attracts *Aedes albopictus*. The attractiveness is 2 to 4 times greater than when using gel L(+)-lactic acid alone or ammonium bicarbonate alone as the attractant and 6 to 13 times greater than using $CO_2$ only.

The test was conducted in Harris County, Texas from August to September in 2003. *Aedes albopictus* is the dominant mosquito species active in the region. Pro traps that release carbon dioxide gas with different attractants were used in the test and each trap was rotated every 24 hours between 6 sites. The mosquitoes caught in each trap were collected every 24 hours. The sample according to the invention was a combination of a cartridge containing the lactic acid gel and a sealed porous bag containing ammonium bicarbonate powder. The lactic acid gel cartridge and ammonium bicarbonate powder alone were also used as attractants for comparison.

Table 6 lists the average daily catch of *Aedes albopictus* with a combination according to the invention, lactic acid gel cartridge alone, ammonium bicarbonate only and $CO_2$ only in Pro traps during two testing periods. Table 7 compares the ratio of the daily catch between the combination lure, and lactic acid, ammonium bicarbonate and $CO_2$ only.

TABLE 6

Average daily catch of *Aedes albopictus*

|  | Aug. 22-27 | Sep. 6-11 |
|---|---|---|
| Combination lure | 180 | 138 |
| Ammonium bicarbonate | 80 | 78 |
| Lactic acid gel | 61 | 79 |
| $CO_2$ | 13 | 21 |

TABLE 7

Comparison between average daily catch of *Aedes albopictus*

| Catch ratio | Aug. 22-27 | Sep. 6-11 | Average |
|---|---|---|---|
| Combination vs. Ammonium bicarbonate | 2.2 | 1.8 | 2.0 |
| Combination vs. lactic acid gel | 3.0 | 1.7 | 2.4 |
| Combination vs. $CO_2$ | 14 | 7 | 10.5 |

As seen in the above tables the attractiveness of the combination lure to *Aedes albopictus* is 2 times that of ammonium bicarbonate, about 2.5 times that of lactic acid gel alone and 10.5 times that of $CO_2$.

The population of *Aedes albopictus* in Harris County dropped dramatically after a hurricane swept across this area in the middle of July 2003. In a test performed at the same sites with attractants of L(+)-lactic acid gel type during the early part of July (Jul. 5-10, 2003) the daily catch of *Aedes albopictus* was from hundreds to thousands (up to 7220 daily). And it is expected that the daily catch of *Aedes albopictus* could be thousands, in highly active mosquito areas, using our Mosquito Magnet® traps with the combined lactic acid/ammonia lure as the attractant in accordance with embodiments of the present invention.

EXAMPLE 2

This example demonstrates that the combination lure according to the present invention is highly attractive to *Culex quinquefasciatus* and the attractiveness is 9 to 50 times greater than that of 1-octen-3-ol when used as the attractant.

The test was conducted in the Sao Paulo area of Brazil from Sep. 19 to Oct. 12 in 2003 with *Culex quinquefasciatus* as the main active mosquito species. The combination lure and other attractants were tested in the Mosquito Magnet® Liberty and Defender traps that release carbon dioxide together with attractant loaded in each trap. The same samples used in Example 1 were used in this example. The attractant 1-Octen-3-ol cartridge was tested as a comparison. The mosquitoes caught in the traps were collected every 48 to 72 hours and the traps were rotated between the test sites after mosquitoes were collected. Table 8 lists the test results (as daily-catch) with the Liberty and Defender when using the combination lure and 1-octen-3-ol as separate attractants and also compared the average daily catch of mosquitoes between the two attractants. It is clear that the combination lure according to the embodiments of the present invention was highly attractive to *Culex quinquefasciatus* and that the attractiveness was about 9 to 51 times greater than that of 1-octen-3-ol when used as the attractant under the same test conditions.

TABLE 8

Comparison of Daily Catch of Female *Culex quinquefasciatus* Between Combined lure and 1-Octen-3-ol (Sao Paulo, Brazil, 2003)

|  | Liberty | | Defender | |
|---|---|---|---|---|
| Date | Lactic acid gel plus ammonium bicarbonate | 1-Octen-3-ol | Lactic acid gel plus ammonium bicarbonate | 1-Octen-3-ol |
| Sep. 19-21 | 523 | 270 | 821 | 4 |
| Sep. 22-23 | 309 | 17 | 207 | 3 |
| Sep. 24-25 | 53 | 4 | 367 | 0 |
| Sep. 26-28 | 86 | 1 | 197 | 6 |
| Sep. 29-30 | 68 | 6 | 86 | 2 |
| Oct. 1-2 | 2 | 5 | 92 | 4 |
| Oct. 3-5 | 319 | 2 | 1105 | 3 |
| Oct. 6-7 | 826 | 7 | 355 | 53 |
| Oct. 8-9 | 482 | 12 | 1162 | 107 |
| Oct. 10-12 | 264 | 12 | 5376 | 10 |
| Daily Average | 293 | 34 | 977 | 19 |
| Lactic acid gel plus ammonium bicarbonate | 8.6 | | 51 | |

TABLE 8-continued

Comparison of Daily Catch of Female *Culex quinquefasciatus* Between Combined lure and 1-Octen-3-ol (Sao Paulo, Brazil, 2003)

| | Liberty | | Defender | |
|---|---|---|---|---|
| Date | Lactic acid gel plus ammonium bicarbonate | 1-Octen-3-ol | Lactic acid gel plus ammonium bicarbonate | 1-Octen-3-ol |
| vs. 1-Octen-3-ol | | | | |

EXAMPLE 3

This example demonstrates that the combination lure according to embodiments of the invention is attractive to *Ochlerotatus canadensis, Anopheles punctipennis* and *Aedes vexans* and the attractiveness to those mosquito species is comparable or better than using 1-octen-3-ol as the attractant.

The test was conducted at the Great Swamp area of North Kingstown, R.I. from Sep. 5 to Sep. 24, 2003. *Ochlerotatus canadensis, Anopheles punctipennis* and *Aedes vexans* were the main species collected amongst the 14 identified mosquito species. Pro traps that release $CO_2$ plus an attractant to be evaluated were used in this testing. The samples of the combination were, again, the combination of a lactic acid gel cartridge and ammonium bicarbonate powder sealed in a porous bag as in Examples 1 and 2. The mosquitoes caught in the traps were collected every 48 to 72 hours and the traps were rotated between the test sites after mosquitoes were collected. Table 9 lists the test results (as daily-catch) when using either the combination lure or 1-octen-3-ol as separate attractants and compared the average daily catch of mosquitoes between the two attractants. Results showed that the attractiveness of the combination of lactic acid and ammonia (as ammonium carbonate) to *Ochlerotatus canadensis, Anopheles punctipennis* and *Aedes vexans* is comparable or better than that of using 1-octen-3-ol as the attractant.

TABLE 9

Comparison of Daily Mosquito Catch between Lactic acid/ammonia combination and 1-Octen-3-ol (Great Swamp, RI, 2003)

| Date | Lactic acid gel plus ammonium bicarbonate | 1-Octen-3-ol |
|---|---|---|
| Sep. 5-8 | 979 | 683 |
| Sep. 8-10 | 317 | 456 |
| Sep. 10-12 | 471 | 301 |
| Sep. 12-15 | 284 | 419 |
| Sep. 15-17 | 461 | 336 |
| Sep. 17-19 | 273 | 306 |
| Sep. 19-22 | 86 | 172 |
| Sep. 22-24 | 86 | 178 |
| Daily Average | 370 | 350 |

EXAMPLE 4

This example demonstrates that the combination lure according to the invention is effectively attractive to *Aedes albopictus* and other mosquito species and the attractiveness to *Aedes albopictus* was three times greater than that of 1-octen-3-ol and 2.5 times greater than that of lactic acid gel when used as the attractant.

The test was done in Waipahu, Hi. in December 2003. The package was constructed substantially as shown in FIG. 11 and included a combined lure of lactic acid gel in the first chamber and molded granules of ammonium carbonate in the second chamber.

The combined lure was evaluated and the attractiveness to mosquitoes was compared with 1-octen-3-ol, lactic acid gel alone and other attractants in Pro traps that release $CO_2$ during testing. The mosquitoes caught in each trap were collected every 24 hours. The daily-catch rate of *Aedes albopictus* and total mosquitoes was counted separately and results for the combined lure, lactic acid gel alone, and 1-octen-3-ol are listed in the following tables 10 and 11. The combined lure was more attractive to *Aedes albopictus* and other mosquito species, than using 1-octen-3-ol or lactic acid gel as the attractant.

TABLE 10

Comparison of mosquito catch between combined lure and 1-octen-3-ol

| | Lactic acid gel plus ammonium bicarbonate | | 1-Octen-3-ol | |
|---|---|---|---|---|
| Date | Total mosquito | *Aedes albopictus* | Total mosquito | *Aedes albopictus* |
| Dec. 12-13 | 190 | 38 | 126 | 7 |
| Dec. 14-15 | 294 | 158 | 32 | 5 |
| Dec. 16-17 | 107 | 59 | 123 | 24 |
| Dec. 18-19 | 161 | 73 | 98 | 35 |
| Dec. 20-21 | 117 | 15 | 64 | 40 |
| Daily Average | 174 | 69 | 89 | 22 |
| Lactic acid gel plus ammonium bicarbonate vs. 1-octen-3-ol | 1.95 | 3.1 | | |

TABLE 11

Comparison of mosquito catch between combined lure (lactic acid gel plus ammonium bicarbonate) and Lactic Acid Gel

| | Lactic acid gel plus ammonium bicarbonate | | Lactic acid gel | |
|---|---|---|---|---|
| Date | Total mosquito | *Aedes albopictus* | Total mosquito | *Aedes albopictus* |
| Dec. 12-13 | 190 | 38 | 131 | 24 |
| Dec. 14-15 | 294 | 158 | 93 | 51 |
| Dec. 16-17 | 107 | 59 | 43 | 11 |
| Dec. 18-19 | 161 | 73 | 25 | 2 |
| Dec. 20-21 | 117 | 15 | 83 | 49 |
| Daily Average | 174 | 69 | 75 | 27 |
| Lactic acid gel plus ammonium bicarbonate vs. Lactic acid gel | 2.3 | 2.5 | | |

CONCLUSION

These studies demonstrate that the combined lactic acid and ammonia lure according to the invention is effectively attractive to varied mosquito species that include *Aedes albopictus, Culex quinquefasciatus, Ochlerotatus canadensis* and other species. The attractiveness of the combined lure to those mosquito species is higher than that of 1-octen-3-ol and lactic acid gel, alone.

The present invention can provide mosquito control measures that are non-toxic or lower in toxicity than currently available products.

It will be appreciated that embodiments of the present invention have been fully and effectively described. The foregoing specific embodiments have been provided to illustrate the structural and functional principles of the present invention, and are not intended to be limiting. To the contrary, the present invention is intended to encompass all modifications, alterations and substitutions within the spirit and scope of the detailed description.

What is claimed is:

1. A lure for attracting flying insects selected from the group of species consisting of *Aedes aegypti, Aedes albopictus, Aedes vexans, Anopheles atropos, Anopheles crucians, Anopheles punctipennis, Anopheles walkeri, Culex erraticus, Culex nigripalpus, Culex pipiens, Culex quinquefasciatus, Culex salinarius, Culiseta melanura, Ochlerotatus canadensis, Ochlerotatus fulvus-pallens, Ochlerotatus infirmatus, Ochlerotatus intrudens, Ochlerotatus triseriatus*, and *Psorophora ferox*, comprising:
   (1) a first chemical attractant, containing a solution of lactic acid in a carrier, wherein the carrier is selected from the group consisting of a polymeric gel and a porous material; and
   (2) a second chemical attractant, containing a source of ammonia;
   said first and second attractants being physically isolated from each other prior to use of the lure, and being disposed in a gaseous carrier to release lactic acid at a rate of about 1 mg/hr to about 30 mg/hr.

2. The lure according to claim 1, wherein the lure further comprises at least a first chamber and a second chamber, and further wherein the first attractant is housed in the first chamber and the second attractant is housed in the second chamber.

3. The lure according to claim 2, the lure further having at least one opening for passage of a gaseous carrier in contact with each of the first and second chambers, whereby the lactic acid from the first chamber and ammonia gas from the second chamber may be dispensed from said chambers in said gaseous carrier.

4. The lure according to claim 2, the lure further having sufficient openings in the chambers to permit passage of separate gaseous carriers to contact the first and second chambers separately, whereby the lactic acid from the first chamber and ammonia gas from the second chamber may be dispensed from said chambers in said gaseous carriers.

5. The lure according to any of claims 3-4, wherein at least one of the gaseous carriers is a flowing gas stream.

6. A device comprising a lure according to claim 5 and a source of carbon dioxide, wherein the source of carbon dioxide is capable of supplying carbon dioxide to the flowing gas stream.

7. The lure according to any of claims 3-4 wherein the gaseous carriers are ambient air flowing by diffusion.

8. A lure for attracting flying insects selected from the group of species consisting of *Aedes aegypti, Aedes albopictus, Aedes vexans, Anopheles atropos, Anopheles crucians, Anopheles punctipennis, Anopheles walkeri, Culex erraticus, Culex nigripalpus, Culex pipiens, Culex quinquefasciatus, Culex salinarius, Culiseta melanura, Ochlerotatus canadensis, Ochlerotatus fulvus-pallens, Ochlerotatus infirmatus, Ochlerotatus intrudens, Ochlerotatus triseriatus*, and *Psorophora ferox*, comprising:
   (1) a first chemical attractant, comprising a solution of lactic acid; and
   (2) a second chemical attractant, comprising a source of ammonia;
   wherein the first and second attractants are physically isolated from each other prior to use of the lure, and wherein the lure is capable of providing effective amounts of lactic acid and ammonia continuously for at least an extended period of time, and
   further wherein the extended period of time is one week, and further wherein the lure is disposed in a gaseous carrier to release lactic acid at a rate of about 1 mg/hr to about 30 mg/hr.

9. The lure according to claim 8, wherein the lactic acid solution is within a first carrier and the carrier is selected from the group consisting of a polymeric gel and a porous material.

10. The lure according to claim 9, wherein the first carrier is a polymeric gel and further wherein a second polymeric gel carrier comprising water is in contact with the first carrier.

11. The lure according to claim 8, wherein the extended period of time is selected from the group consisting of two weeks, three weeks, four weeks, six weeks, eight weeks, ten weeks, and twelve weeks.

12. The lure according to claim 8, wherein the extended period of time is three weeks.

13. The lure according to claim 1, wherein the lure is at least 50% more effective in attracting flying insects than a comparable lure having one of the first and second chemical attractants but not both the first and the second chemical attractant.

14. The lure according to claim 13, wherein the effectiveness of the lure is measured against the comparable lure such that both the lure and the comparable lure are tested in combination with comparable sources of carbon dioxide.

15. The lure according to claim 13, wherein the lure is at least 100% more effective than the comparable lure.

16. The lure according to claim 13, wherein the lure is at least 200% more effective than the comparable lure.

17. The lure according to claim 13, wherein the lure is at least 300% more effective than the comparable lure.

18. The lure according to claim 13, wherein the lure is at least 400% more effective than the comparable lure.

19. The lure according to claim 13, wherein the lure is at least 500% more effective than the comparable lure.

20. The lure according to claim 8, wherein the lure is at least 50% more effective in attracting flying insects than a comparable lure having the first chemical attractant but omitting the second chemical attractant, wherein the increased effectiveness is measured as an average over the course of the extended period of time.

21. The lure according to claim 20, wherein the effectiveness of the lure is measured against the comparable lure such that both the lure and the comparable lure are tested in combination with comparable sources of carbon dioxide.

22. The lure according to claim 20, wherein the lure is at least 100% more effective than the comparable lure.

23. The lure according to claim 20, wherein the lure is at least 200% more effective than the comparable lure.

24. The lure according to claim 23, wherein the lure is at least 300% more effective than the comparable lure.

25. The lure according to claim 24, wherein the lure is at least 400% more effective than the comparable lure.

26. The lure according to claim 25, wherein the lure is at least 500% more effective than the comparable lure.

27. The lure of claim 8, wherein the effective amount of the ammonia released from the second chemical attractant is about 1 mg/hr to about 30 mg/hr.

28. The lure of claim 27, wherein the lure is suitable for use indoors.

29. The lure of claim 27, wherein the effective amount of the lactic acid released from the first chemical attractant is about 2 mg/hr to about 30 mg/hr, and the effective amount of the ammonia released from the second chemical attractant is about 2 mg/hr to about 130 mg/hr.

30. The lure of claim 29, wherein the effective amount of the lactic acid is about 3 mg/hr to about 30 mg/hr.

31. The lure of claim 29, wherein the effective amount of the ammonia is about 3 mg/hr to about 130 mg/hr.

32. The lure of claim 8, wherein the lure, when contacted with a flow of gas including an elevated level of carbon dioxide gas at a temperature of about 90° F., is capable of releasing ammonia at rates within the range of about 3 mg/hr to about 30 mg/hr, and further is capable of releasing lactic acid at rates within the range of about 1 mg/hr to 20 mg/hr continuously for the extended period of time.

33. The lure of claim 32, wherein the extended period of time is at least two weeks.

34. The lure of claim 33, wherein the extended period of time is at least three weeks.

35. The lure according to claim 1, wherein the source of ammonia is a solid.

36. The lure according to claim 1, wherein the source of ammonia is a cylinder of compressed ammonia gas.

37. The lure according to claim 1, wherein the source of ammonia is a liquid.

38. The lure according to claim 1, wherein the source of ammonia gas comprises ammonium bicarbonate.

39. The lure according to claim 1, wherein the source of ammonia gas comprises an intimate mixture of an ammonium salt and a strong base.

40. The lure according to claim 1, wherein the source of ammonia is an ammonium compound which is capable of generating ammonia gas when heated.

41. The lure according to claim 1, wherein the source of ammonia is an ammonium compound which is capable of generating ammonia gas upon exposure to a warm flow of carbon dioxide gas.

42. The lure according to claim 38, wherein the source of ammonia further comprises a binder mixed with the ammonium bicarbonate, and further wherein the source of ammonia is in the form of granules, a viscous liquid, a wax, or a combination thereof.

43. The lure according to claim 42, wherein the source of ammonia is molded into a form.

44. The lure according to claim 42, wherein the source of ammonia comprises from about 50% to about 90% by weight of ammonium bicarbonate, from about 5 to about 35% binder, and from about 3 to about 20% by weight of water.

45. The lure according to claim 42, wherein the binder comprises starch.

46. The lure according to claim 38, wherein the second attractant comprises a molded composition having a form which is a cylindrical shape or which is a longitudinal fraction of a cylindrical shape.

47. The lure according to claim 46, wherein the molded composition weighs from about 3 to about 50 grams.

48. The lure according to claim 47, wherein the lure is suitable for use indoors and the molded composition weighs between about 3 and about 25 grams.

49. The lure according to claim 47, wherein the lure is adapted for use outdoors and the molded composition weighs between about 30 grams and about 50 grams.

50. The lure according to claim 38, wherein the second chemical attractant comprises from about 5 to about 15 grams ammonium bicarbonate for each week the lure is capable of continuously supplying an effective amount of ammonia.

51. The lure according to claim 46, wherein the diameter of the cylindrical shape is within the range of about 1.0 inches to about 1.5 inches.

52. The lure according to claim 51, wherein the molded composition has a length of from about 1.5 inches to about 3.5 inches.

53. The lure according to claim 36, wherein the diameter of the cylindrical shape is within the range of about 0.8 inches to about 1.3 inches, and further wherein the lure is suitable for use indoors.

54. The lure according to claim 52, wherein the molded composition has a length of from about 1.0 inches to about 2.0 inches.

55. The lure according to claim 46, wherein the carrier of the first chemical attractant is a polymeric gel.

56. The lure according to claim 55, wherein the first chemical attractant has a form which is a longitudinal fraction of a cylindrical shape, the second chemical attractant has a form which is a longitudinal fraction of a cylindrical shape, and the forms of the first and second attractants are arranged adjacent to one another so as to define a cylindrical shape.

57. The lure according to claim 55, wherein the first and second attractants have substantially the same diameter and substantially the same length.

58. The lure according to claim 38, wherein the ammonium bicarbonate is a food grade ammonium bicarbonate.

59. The lure according to claim 38, wherein the ammonium bicarbonate has a purity of at least 99%.

60. The lure according to claim 1, wherein the lactic acid comprises food grade L(+)-lactic acid.

61. The lure according to claim 1, wherein the lactic acid has a stereochemical (L-isomer) purity of at least about 95%.

62. The lure according to claim 1, wherein the carrier of the first chemical attractant is a polymeric gel and the lactic acid is about 1 wt % to about 99 wt % of the first chemical attractant.

63. The lure according to claim 62, wherein the lactic acid is about 25 wt % to about 90 wt % of the first chemical attractant.

64. The lure according to claim 63, wherein the lactic acid is about 25 wt % to about 60 wt % of the first chemical attractant.

65. The lure according to claim 64, wherein the lactic acid is about 30 wt % to about 40 wt % of the first chemical attractant.

66. The lure according to claim 65, wherein the lactic acid is about 34 wt % to about 37 wt % of the first chemical attractant.

67. The lure according to claim 62, wherein the source of ammonia is ammonium bicarbonate and the ammonium bicarbonate is 25 wt % to about 99 wt % of the second chemical attractant.

68. The lure according to claim 64, wherein the source of ammonia is ammonium bicarbonate and the ammonium bicarbonate is about 50 wt % to about 90 wt % of the second chemical attractant.

69. The lure according to claim 65, wherein the source of ammonia is ammonium bicarbonate and the ammonium bicarbonate is about 70 wt % to about 80 wt % of the second chemical attractant.

70. The lure according to claim 66, wherein the source of ammonia is ammonium bicarbonate and the ammonium bicarbonate is 72 wt % to about 78 wt % of the second chemical attractant.

71. A lure for attracting flying insects selected from the group of species consisting of *Aedes aegypti, Aedes albopictus, Aedes vexans, Anopheles atropos, Anopheles crucians, Anopheles punctipennis, Anopheles walkeri, Culex erraticus, Culex nigripalpus, Culex pipiens, Culex quinquefasciatus, Culex salinarius, Culiseta melanura, Ochlerotatus canaden-*

*sis, Ochlerotatus fulvus-pallens, Ochlerotatus infirmatus, Ochlerotatus intrudens, Ochlerotatus triseriatus*, and *Psorophora ferox*, comprising:

(1) a first chemical attractant, containing a solution of lactic acid in a carrier, wherein the carrier is selected from the group consisting of a polymeric gel and a porous material which releases lactic acid at a rate of about 2 mg/hr to about 30 mg/hr; and (2) a second chemical attractant, containing a source of ammonia;

said first and second attractants being physically isolated from each other prior to use of the lure.

72. The lure according to claim 71, wherein the carrier releases lactic acid at a rate of about 3 mg/hr to about 30 mg/hr.

73. The lure according to claim 71, wherein the lure further comprises at least a first chamber and a second chamber, and further wherein the first attractant is housed in the first chamber and the second attractant is housed in the second chamber.

74. The lure according to claim 73, the lure further having at least one opening for passage of a gaseous carrier in contact with each of the first and second chambers, whereby the lactic acid from the first chamber and ammonia gas from the second chamber may be dispensed from said chambers in a gaseous carrier.

75. The lure according to claim 73, the lure further having sufficient openings in the chambers to permit passage of separate gaseous carriers to contact the first and second chambers separately, whereby the lactic acid from the first chamber and ammonia gas from the second chamber may be dispensed from said chambers in said gaseous carriers.

76. The lure according claim 74, wherein the gaseous carrier is a flowing gas stream.

77. The lure according claim 75, wherein the gaseous carriers are flowing gas streams.

78. A device comprising a lure according to claim 74 and a source of carbon dioxide, wherein the source of carbon dioxide is capable of supplying carbon dioxide to the flowing gas stream.

79. A device comprising a lure according to claim 75 and a source of carbon dioxide, wherein the source of carbon dioxide is capable of supplying carbon dioxide to the flowing gas streams.

80. The lure according to claim 74, wherein the gaseous carrier is ambient air flowing by diffusion.

81. The lure according to claim 75, wherein the gaseous carriers are ambient air flowing by diffusion.

* * * * *